US006642409B2

(12) United States Patent
Ishii et al.

(10) Patent No.: US 6,642,409 B2
(45) Date of Patent: Nov. 4, 2003

(54) PROCESS FOR PRODUCING 4,4,4-TRIFLUORO-3-HYDROXYBUTYRIC ACID DERIVATIVES

(75) Inventors: Akihiro Ishii, Saitama (JP); Masatomi Kanai, Saitama (JP); Takashi Hayami, Saitama (JP); Katsuyoshi Shibata, Aichi (JP); Masaki Matsui, Gifu (JP); Kazumasa Funabiki, Aachen (DE); Yokusu Kuriyama, Saitama (JP); Manabu Yasumoto, Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/770,671

(22) Filed: Jan. 29, 2001

(65) Prior Publication Data

US 2002/0016511 A1 Feb. 7, 2002

(30) Foreign Application Priority Data

| | | |
|---|---|---|
| Jan. 27, 2000 | (JP) | 2000-019156 |
| Jan. 27, 2000 | (JP) | 2000-019165 |
| Feb. 10, 2000 | (JP) | 2000-034026 |
| Jun. 27, 2000 | (JP) | 2000-193316 |
| Jul. 10, 2000 | (JP) | 2000-208742 |
| Oct. 17, 2000 | (JP) | 2000-317069 |

(51) Int. Cl.[7] ........................ C07C 69/93; C07C 69/100
(52) U.S. Cl. ........................ 560/227; 560/129; 560/226; 568/324
(58) Field of Search .......................... 568/324; 560/227, 560/129, 226

(56) References Cited

U.S. PATENT DOCUMENTS

| | | |
|---|---|---|
| 5,118,836 A | 6/1992 | Tanida |
| 5,716,841 A | 2/1998 | Tixidre |

FOREIGN PATENT DOCUMENTS

| | | |
|---|---|---|
| DE | 4207261 | 9/1993 |
| EP | 424244 | 4/1991 |
| EP | 0427396 | 5/1991 |
| EP | 0736606 | 2/1998 |
| JP | 64003154 | 1/1989 |
| JP | 3176450 | 7/1991 |
| JP | 8289799 | 2/1998 |
| WO | WO9942590 | 8/1999 |

OTHER PUBLICATIONS

Seebach et al, Helvetica Chimica Acta, vol. 67, (1984) pp. 1843–1853.*

Pasto et al, Experiments and Techniques in Organic Chemistry, 1992, pp. 43 to 46.*

Seebach et al, Helvetica Chimica Acta, vol. 67, pp. 1843–1853, 1984.*

Pasto et al, Experiment and Techniques in Organic Chemistry, Chapter 2, pp43 to 46.*

Seebach et al, Helvetica Chimica Acta, vol. 67, pp1843–1853, 1984.*

C. Schmit, et al., "Vicinal Alkylation of Alkynes, A Short Route Toward $\Delta^{\alpha,\beta}$ Butenolides, Furans and Cyclopentenones" Telrahedron Letters, vol. 25, No. 44, pp. 5043–5046, 1984.

Paul A. Grieco, "Conversion of Ketones into Lactones with Benzeneseleninic Acid and Hydrogen Peroxide (Benzeneperoxyseleninic Acid) : A New Reagent for the Baeyer–Villiger Reaction" J.C.S. Chemistry, 1977.

Dieter Seebach, "214. Preparation by Yeast Reduction and Determination of the Senses of Chirality of Enantiomerically Pure Ethyl (–)–4,4,4–Trichloro–3–hydroxy–and (+)–4,4,4–Trifluoro–3–hydroxybutanoate" Helvetica Chimica Acta, vol. 67, 1984.

R.R. Sauers, "The Importance of Steric Effects in the Baeyer–Villiger Oxidation" J.Am.Chem.Soc., vol. 83, pp.27359–2762, 1961.

Julius Schmidlin, "Phosphormononpersaure and Uberphosphorsaure" Chem. Ber., 43, pp. 1162–1171, 1910.

Jenq Tain Lin, "A Microbially Based Approach for the Preparation of Chiral Molecules Possessing the Trifluoromethyl Group" American Chemical Society, vol. 87, 1987.

(List continued on next page.)

*Primary Examiner*—Alan L. Rotman
*Assistant Examiner*—Héctor M Reyes
(74) *Attorney, Agent, or Firm*—Crowell & Moring LLP

(57) ABSTRACT

A first process for producing an optically active perfluoroalklylcarbinol derivative includes (a) reacting an optically active imine with a compound that is a hemiacetal of a perfluoroalkylaldehyde or a hydrate of a perfinoroalkylaldehyde to obtain a condensate; and (b) hydrolyzing the condensate under an acid condition. A second process for increasing optical purity of an optically active 4,4,4-trifluoro-3-hydroxy-1-aryl-1-butanone derivative includes (a) precipitating a racemic crystal of the derivative, from the derivative; and (b) removing the racemic crystal from the derivative. A third process for increasing optical purity of the butanone derivative (includes recrystallizing the derivative. Novel compounds are optically active and inactive 4,4,4-trifluoro-3-hydroxybotanoic aryl ester derivatives. A fourth or fifth process for producing an optically active and inactive 4,4,4-trifloro-3-hydroxybutyric acid aryl ester derivative includes oxidizing an optically active or optically inactive 4,4,4-trifluoro-3-hydroxy-1-aryl-1-butanone derivative. A sixth process for increasing optical purity of the optically active aryl ester derivative includes recrystallizing the derivative. A seventh process for producing an optically active 4,4,4-trifluoro-3-butanediol includes reducing the optically active aryl ester derivative by a hydride. An eighth or ninth process for producing an optically active or inactive 4,4,4-trifluoro-3-hydroxybutyric acid alkyl ester derivative includes reacting under an acid condition the optically active or optically inactive aryl ester derivative with a lower alcohol. It is possible to suitably combine at least two of the first to ninth processes.

21 Claims, No Drawings

OTHER PUBLICATIONS

Toshio Kubota, "Facile Synthesis of α–Trifluoromethylated Alcohols from Trifluoroacetaldehyde Ethyl Hemiacetal" Tetrahedrom Letters, vol. 33, No. 10, pp. 1351–1354, 1992.

Teck–Peng LOH, "A versatile and practical synthesis of α–trifluoromethylated alchols from trifluoroacetaldehyde ethyl hemiacetal in water" Chemistry Communication, 1996.

Kazumasa Funabiki, "Enamine–assisted facile generation of trifluoroacetaldehyde from trifluoroacetaldehyde ethyl hemiacetal and its carbon–carbon bond forming reaction leading to β–hydroxy–β–trofluoromethyl ketones" Chemistry Communication, 1998.

Kazumasa Funabibki, "Efficient Generation of Trifluoroacetaldehyde and Successive Reaction with Imines Affording β–hydroxy–β–trofluoromethyl Ketones" Synlett, No. 9, pp. 1477–1479, 1999.

Gerrit Toennies, "A New Method for the Preparatin of Permonophosphoric Acid" Contribution from the Lankenau Hospital Research Institute.

Yoshiro Ogata, "Kinetics of the Baeyer–Villiger Reaction of Acetophenones with Permonophosphoric Acid" J.Org. Chemistry, vol.43, No. 12, 1978.

* cited by examiner

PROCESS FOR PRODUCING 4,4,4-TRIFLUORO-3-HYDROXYBUTYRIC ACID DERIVATIVES

BACKGROUND OF THE INVENTION

The present invention relates to processes for producing 4,4,4-trifluoro-3-hydroxybutyric acid derivatives. The present invention relates particularly to a process for producing optically active 4,4,4-trifluoro-3-hydroxybutyric acid ester derivatives, which are important intermediates for medicines, agricultural chemicals and functional materials such as ferroelectric liquid crystal. The present invention further relates particularly to a process for producing optically active 4,4,4-trifluoro-1,3-butanediol, which is also an important intermediate for medicines and agricultural chemicals.

There are several conventional processes for producing 4,4,4-trifluoro-3-hydroxybutyric acid ester derivatives. Each of Japanese Patent Laid-open Publication JP-A-64-3154 and EP-A-0424244 discloses an optical resolution of a diastereoisomer salt of optically active α-phenyl ethyl amine and 4,4,4-trifluoro-3-hydroxybutyric acid through recrystallization. JP-A-8-289799, corresponding to U.S. Pat. No. 5,716,841 and EP-0736606-A1, discloses an optical resolution of 4,4,4-trifluoro-3-hydroxybutyric acid ethyl ester through an asymmetric hydrolysis of lipase. There is a recent demand for a process for easily and efficiently producing optically active 4,4,4-trifluoro-3-hydroxybutyric acid ester derivatives.

Baeyer-Villiger oxidation is generally known as a common process for producing esters. In this oxidation, corresponding ketones are reacted with an oxidizing agent, thereby introducing oxygen atom to the ketone's one side having more substituents than those of the other side. Examples of such oxidizing agent are m-CPBA (Tetrahedron Lett., 25, 5043 (1984)), benzeneperoxyseleninic acid (J. Chem. Soc., Chem. Commun., 870 (1977)) and trifluoroperacetic acid (J. Am. Chem. Soc., 83, 2759 (1961)). It is important to select an optimum oxidizing agent in Baeyer-Villiger oxidation. The selection of an optimum oxidizing agent depends on distortion of the ketones and substituent transfer capability. Furthermore, it is necessary to consider the effect on other functional groups in the same molecule and decomposition such as tar formation by an excessive oxidation. In particular, if an optically active ketone is used as a raw material, it is important that the stereochemistry is maintained before and after the reaction.

JP-A-8-151348 discloses a process for producing an optically active fluorine-containing 3-hydroxybutyric acid ester by an ester exchange reaction between an alcohol and an optically active fluorine-containing 3-hydroxybutyric acid ethyl ester in the presence of an ammonium salt of sulfonic acid.

Helvetica Chimica Acta, 67, 1843, 1984 discloses a process for improving optical purity of 4,4,4-trifluoro-3-hydroxybutyric acid ethyl ester. In this process, optical purity of the mother liquor is improved by the selective precipitation of racemic crystals in recrystallization. The precipitated racemic crystal has a melting point of 16° C. and is in the form of oil at room temperature. Therefore, it is necessary to conduct sequential operations, such as recrystallization and filtration, under a low temperature. The publication further discloses another process, in which 3,5-dinitrobenzoate form of 4,4,4-trifluoro-3-hydroxybutyric acid ethyl ester is recrystallized, thereby improving the optical purity. In this process, it is necessary to induce ester from alcohol and to conduct hydrolysis after the purification.

J. Org. Chem., 52, 3211, 1987 discloses a process for asymmetrically hydrolyzing (±)-4,4,4-trifluoro-3-acetoxybutyric acid ethyl ester by lipase. This process requires a large amount of a high-price enzyme.

The above-mentioned process, which is disclosed in U.S. Pat. No. 5,716,841, also requires a large amount of a high-price enzyme. This publication further discloses a reduction of the unreacted (R)-4,4,4-trifluoro-3-hydroxybutyric acid ethyl ester by sodium borohydride, thereby producing an optically active diol.

The above-mentioned resolution, which is disclosed in EP-A-0424244, requires the use of a high-price resolution agent. Furthermore, it is necessary to conduct several operations, such as neutralization and extraction, in order to regenerate optically active 4,4,4-trifluoro-3-hydroxybutyric acid.

Recently, there have been active researches for providing medicines, agricultural chemicals and various functional materials, such as ferroelectric liquid crystal, with unique physiological activity and physical characteristics by introducing perfluoroalkyl group into a particular site. Perfluoroalkylaldehyde can be used as a synthon for constructing a perfluoroalkrylcarbinol derivative. In particular, an asymmetric reaction using a perfluoroalkylaldehyde can be used for easily and efficiently synthesizing an optically active perfluoroalkylcarbinol derivative. For example, it becomes possible to obtain an optically active trifluoromethylcarbinol derivative by (a) reacting α-methoxystyrene derivative with fluoral in the presence of an optically active binaphthol-titanium complex, thereby obtaining a product corresponding to that of Friedel-Crafts reaction, and then by (b) hydrolyzing the product under an acid condition. Perfluoroalkylaldehyde is, however, low in boiling point and highly reactive. Therefore, it easily polymerizes by itself and thereby its handling is difficult. Thus, it is usual to stabilize perfluoroalkylaldehyde in the form of hemiacetal or hydrate.

Upon heating, the stabilized periluoroalkylaldehyde is dropped to concentrated sulfuric acid or phosphorus pentoxide, and the resulting gas is used in the above reaction. However, the generated perfluoroalkylaldehyde tends to polymerize partially or remain in the acid. Therefore, it is necessary to use an excessive amount of hemiacetal or hydrate. Furthermore, post-treatment of the acid used in an excessive amount may become a problem. Thus, the use of perfluoroalkylaldehyde for producing an optically active perfluoroalkylcarbinol derivative may be impractical in an industrial production.

There are several processes for synthesizing perfluoroalkylcarbinol derivatives by directly reacting perfluoroalkylaldehyde hemiacetal or its hydrate with nucleophiles. In fact, Tetrahedron Lett., 33, 1351 (1992) discloses a synthesis of fluoral ethylhemiacetal and trimethylsilylnitrile in dioxane in the presence of zinc iodide. Chem. Commun., 1996, 1929 discloses a synthesis of fluoral ethylhemiacetal and allylbromide in water in the presence of indium. Chem. Commun., 1998, 2051 and Synlett, 1999, 1477 disclose that a condensation of fluoral ethylhemiacetal or hydrate and enamine or imine proceeds easily in the absence of catalyst, thereby synthesizing 4,4,4-trifluoro-3-hydroxy-1-aryl-1-butanone derivative.

As mentioned above, optically active 4,4,4-trifluoro-1,3-butanediol is an important intermediate for medicines and agricultural chemicals. In particular, its R-form is a partial structure of BEFLOXATONE which is an antidepressant of Synthelabo Co. (EP-0736606-A1).

WO 9942590 discloses a process for producing (R)-4,4,4-trifluoro-3-hydroxybutyric acid ester, which is a precursor of (R)-4,4,4-trifluoro-1,3-butanediol, by an asymmetric reduction of a trifluoroacetoacetate using an enzyme prepared by a recombinant DNA technique. This process requires the use of $NADP^+$, which is very high in price.

SUMMARY OF THE INVENTION

It is an object of the present invention to provide a process for producing an optically active perfluoroalkylcarbinol derivative, which is a precursor of an optically active 3-perfluoroalkyl-3-hydroxypropionic acid derivative.

It is another object of the present invention to provide a process for increasing optical purity of an optically active 4,4,4-trifluoro-3-hydroxy-1-aryl-1-butanone derivative, which is a precursor of an optically active 4,4,4-trifluoro-3-hydroxybutyric acid derivative.

It is still another object of the present invention to provide a process for producing a 4,4,4-trifluoro-3-hydroxybutyric acid aryl ester derivative.

It is a further object of the present invention to provide a process for increasing optical purity of an optically active 4,4,4-trifluoro-3-hydroxybutyric acid aryl ester derivative.

It is a further object of the present invention to provide a process for producing a 4,4,4-trifluoro-3-hydroxybutyric acid alkyl ester derivative.

It is a still further object of the present invention to provide a process for producing an optically active 4,4,4-trifluoro-1,3-butanediol.

According to a first aspect of the present invention, there is provided a first process for producing an optically active perfluoroalkylcarbinol derivative represented by the general formula [1], the first process comprising:

reacting an optically active imine represented by the general formula [2] with a compound represented by the general formula [3], said compound being a hemiacetal of a perfluoroalkylaldehyde or a hydrate of a perfluoroalkylaldehyde, thereby obtaining a condensate between said optically active imine and said compound; and hydrolyzing said condensate under an acid condition, thereby producing said optically active perfluoroalkylcarbinol derivative,

[1]

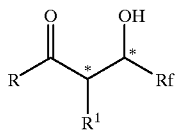

where R is a $C_{1-6}$ aliphatic alkyl group, a $C_{3-8}$ cyclic alkyl group, an unsubstituted or substituted aryl group, or an unsubstituted or substituted heterocyclic group;

$R^1$ is a hydrogen, a $C_{1-6}$ aliphatic alkyl group, a $C_{3-8}$ cyclic alkyl group, a $C_{1-6}$ aliphatic alkoxy group, a $C_{3-8}$ cyclic alkoxy group, an unsubstituted or substituted aryl group, or an unsubstituted or substituted heterocyclic group;

a combination of R and $R^1$ optionally forms (1) a $C_{4-8}$ cyclic alkyl group, (2) a four to eight-membered heterocyclic group containing one or two hetero atoms, or (3) a condensed ring comprising first and second rings fused together, said first ring being said $C_{4-8}$ cyclic alkyl group or said four to eight-membered heterocyclic group, said second ring being an unsubstituted or substituted aryl group or an unsubstituted or substituted heterocyclic group;

Rf represents a perfluoroalkyl group; and the symbol * represents an asymmetric carbon,

[2]

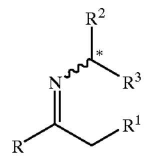

where R, $R^1$, a combination of R and $R^1$, and the symbol * are defined as above;

each of $R^2$ and $R^3$ is independently a $C_{1-6}$ aliphatic alkyl group, a $C_{3-8}$ cyclic alkyl group, an unsubstituted or substituted aryl group, an unsubstituted or substituted heterocyclic group, an alkoxycarbonyl group or a hydroxyalkyl group; and $R^2$ and $R^3$ are not the same substituted groups at the same time,

[3]

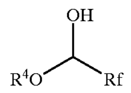

where $R^4$ is a hydrogen, a $C_{1-6}$ aliphatic alkyl group, a $C_{3-8}$ cyclic alkyl group, an unsubstituted or substituted aryl group, or an unsubstituted or substituted heterocyclic group; and Rf is defined as above.

According to a second aspect of the present invention, there is provided a second process for increasing optical purity of an optically active 4,4,4-trifluoro-3-hydroxy-1-aryl-1-butanone derivative represented by the general formula [4], the second process comprising:

precipitating a racemic crystal of said derivative, from said derivative; and removing said racemic crystal from said derivative, thereby improving optical purity of said derivative.

[4]

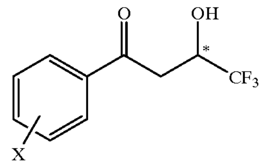

where X is a hydrogen, a $C_{1-6}$ alkyl, a $C_{1-6}$ alkoxy, or a halogen atom selected from the group consisting of F, Cl, Br and I; and the symbol * represents an asymmetric carbon.

According to a third aspect of the present invention, there is provided a third process for increasing optical purity of an optically active 4,4,4-trifluoro-3-hydroxy-1-aryl-butanone derivative represented by the general formula [4]. The third process comprises recrystallizing said derivative, thereby increasing optical purity of said derivative.

According to fourth aspect of the present invention, there is provided an optically active 4,4,4-trifluoro-3-hydroxybutanoic aryl ester derivative represented by the general formula [5],

[5]

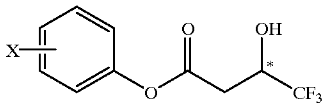

where X and the symbol * are defined as above.

According to the fourth aspect of the present invention, there is provided an optically inactive 4,4,4-trifluoro-3-hydroxybutanoic aryl ester derivative represented by the general formula [6],

[6]

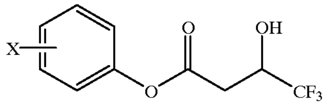

where X is defined as above.

According to the fourth aspect of the present invention, there is provided a fourth process for producing an optically active 4,4,4-trifluoro-3-hydroxybutyric acid aryl ester derivative represented by the general formula [5]. The fourth process comprises oxidizing an optically active 4,4,4-trifluoro-3-hydroxy-1-aryl-1-butanone derivative represented by the general formula [4], thereby achieving Baeyer-Villiger oxidation and producing said aryl ester derivative.

According to the fourth aspect of the present invention, there is provided a fifth process for producing an optically inactive 4,4,4-trifluoro-3-hydroxybutyric acid aryl ester derivative represented by the general formula [6]. The fifth process comprises oxidizing an optically inactive 4,4,4-trifluoro-3-hydroxy-1-aryl-1-butanone derivative represented by the general formula [7], thereby achieving Baeyer-Villiger oxidation and producing said aryl ester derivative,

[7]

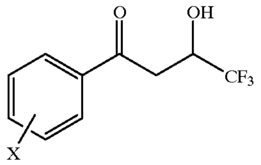

where X is defined as above.

In the fourth and fifth processes, it is possible to achieve Baeyer-Villiger oxidation by using an oxidizing agent such as peroxophosphoric acid or trifluoroperacetic acid.

According to a fifth aspect of the present invention, there is provided a sixth process for increasing optical purity of an optically active 4,4,4-trifluoro-3-hydroxybutanoic aryl ester derivative represented by the general formula [5]. The sixth process comprises recrystallizing said derivative, thereby increasing optical purity of said derivative.

According to a sixth aspect of the present invention, there is provided a seventh process for producing an optically active 4,4,4-trifluoro-1,3-butanediol represented by the general formula [8], said seventh process comprising reducing an optically active 4,4,4-trifluoro-8-hydroxybutyric acid aryl ester represented by the general formula [5] by a hydride, thereby producing said butanediol,

[8]

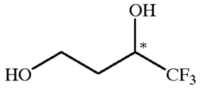

where the symbol * represents an asymmetric carbon.

According to a seventh aspect of the present invention, there is provided an eighth process for producing an optically active 4,4,4-trifluoro-3-hycdroxybutyric acid alkyl ester derivative represented by the general formula [9], said eighth process comprising reacting under an acid condition an optically active 4,4,4-trifluoro-3-hydroxybutyric acid aryl ester derivative represented by the general formula [5], with a lower alcohol represented by the general formula ROH where R is a $C_{1-6}$ alkyl, thereby achieving an ester exchange and producing said alkyl ester derivative,

[9]

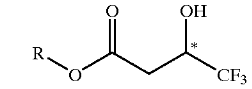

where R is a $C_{1-6}$ alkyl, and the symbol * represents an asymmetric carbon.

According to the seventh aspect of the present invention, there is provided a ninth process for producing an optically inactive 4,4,4-trifluoro-3-hydroxybutyric acid alkyl ester derivative represented by the general formula [10], said ninth process comprising reacting under an acid condition an optically inactive 4,4,4-trifluoro-3-hydrocybutyric acid aryl ester derivative represented by the general formula [6], with a lower alcohol represented by the general formula ROH where R is a $C_{1-6}$ alkyl, thereby achieving an ester exchange and producing said alkyl ester derivative,

[10]

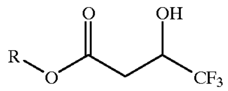

where R is a $C_{1-6}$ alkyl.

According to the present invention, it is possible to suitably combine at least two of the above-mentioned first to ninth processes. For example, it is possible to sequentially combine the first, second, third, fourth, sixth and seventh processes together for producing an optically active 4,4,4-trifluoro-1,3-butanediol represented by the general formula [8]. As another example, it is possible to sequentially combine the first, second, third, fourth, sixth and eighth processes together for producing an optically active 4,4,4-trifluoro-3-hydroxybutyric acid alkyl ester derivative represented by the general formula [9]. As still another example, it is possible to sequentially combine the fifth and ninth processes together for producing an optically inactive 4,4,4-trifluoro-3-hydroxybutyric acid alkyl ester derivative represented by the general formula [10].

DESCRIPTION OF THE PREFERRED EMBODIMENTS

The first process for producing an optically active perfluoroalkylcarbinol derivative represented by the general formula [1] will be described in detail in accordance with the first aspect of the invention, as follows, The reactant, which is a hemiacetal or hydrate of a perfluoroalkylaldehyde, represented by the general formula [3], is stable and easy to be handled.

The optically active imine, which is used in the first process and represented by the general formula [2], can easily and efficiently be produced in an industrial scale by subjecting under an acid condition (a) a ketone represented by the general formula [11] and (b) an optically active primary amine represented by the general formula [12] to dehydration and condensation,

[11]

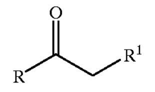

where R, $R^1$ and a combination of R and $R^1$ are defined as in the general formula [1],

[12]

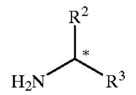

where each of $R^2$ and $R^3$ is defined as in the general formula [2], and $R^2$ and $R^3$ are not the same substituted groups at the same time.

Examples of the ketone represented by the general formula [11] are acetone, methyl ethyl ketone, methyl n-propyl ketone, methyl i-propyl ketone, pinacolin, methyl c-hexyl ketone, acetophenone, 2'-methylacetophenone, 4'-methylacetophenone, 2'-methoxyacetophenone, 4'-methoxyacetophenone, 2'-chloroacetophenone, 4'-chloroacetophenoine, 2'-ethoxycarbonylacetophenone, 4'-ethoxycarbonylacetophenone, 2'-nitroacetophenone, 4'-nitroacetophenone, 2',4',6'-trimethylacetophenone, propiophenone, n-butyrophenone, 2-thienyl methyl ketone, phenyl c-hexyl methyl ketone, phenyl benzyl ketone, phenyl 2-pyridyl methyl ketone, 1-tetralone, and 2-tetralone.

Examples of the optically active primary amine represented by the general formula [12] are 1-phenylethylamine, 1-1'-naphthylethylamine, 1-2'-naphthylethylamine, 1-c-hexylethylamine, phenylglycine methyl ester, valine methyl ester, and phenyl glycynol. Of these, 1-phenylethylamine, 1-1'-naphthylethylamine, 1-2'-naphthylethylamine and phenyl glycynol are preferable. In particular, 1-phenylethylamine and 1-2'-naphthylethylamine are more preferable. The optically active primary amine exists in the R-form or S-form. Therefore, the optically active imine derived from the optically active primary amine also exists in the R-form or S-form. The selection of the enantiomer (R-form or S-form) of the optically active primary amine can be made in accordance with the absolute configuration of the target product.

In the above-mentioned dehydration and condensation, the optically active primary amine is generally reacted in an amount equimolar with the ketone. Therefore, it suffices to use the optically active primary amine in an amount of 1 mole or greater, preferably 1–10 moles, more preferably 1–5 moles, per mol of the ketone. The dehydration and condensation can be conducted under an acid condition by removing water formed as a by-product, from the reaction system.

It is preferable to conduct the dehydration and condensation by removing water formed as a by-product with a Dean-Stark tube, using a solvent that is not miscible with water, that has a specific gravity lower than that of water, and that forms an azeotropic mixture with water. Preferable examples of this solvent are aromatic hydrocarbons such as benzene, toluene, ethylbenzene and xylene. Toluene is particularly preferable. The solvent may be one of these compounds or a mixture of at least two of these compounds. It is necessary to use the solvent in an amount such that the theoretical amount of water produced as a by-product is removed as an azeotropic mixture with the solvent. It is, however, possible to extremely reduce the amount of the solvent by using a Dean-Stark tube.

In the dehydration and condensation, an acid is used for making an acid condition. Examples of this acid are Lewis acids such as zinc chloride, titanium(IV) chloride, aluminum chloride and boron trifluoride; organic acids such as p-toluenesulfonic acid and 10-camphorsulfonic acid; and inorganic acids such as hydrochloric acid, sulfuric acid and phosphoric acid. Of these, zinc chloride and p toluenesulfonic acid preferable. In particular, zinc chloride is more preferable. It suffices to use the acid in a catalytic amount relative to that of the ketone. In fact, this catalytic amount is preferably 0.001–1 mole, more preferably 0.005–0.5 moles, per mole of the ketone. It suffices to conduct dehydration and condensation at a temperature between the boiling point of the azeotropic mixture and the boiling of the solvent. In particular, it is preferably in the vicinity of the boiling point of the solvent.

After the dehydration and condensation, it is possible to conduct a conventional post-treatment, thereby obtaining a crude product of the optically active imine. According to need, this crude product can be subjected to a purification such as the use of activated carbon, distillation, recrystallization, or column chromatography, thereby obtaining the optically active imine of high purity. Alternatively, a reaction liquid after the dehydration and condensation can be used in the first process without conducting the purification of the crude product. In fact, this reaction liquid may be subjected to a washing with a basic aqueous solution of, for example, sodium hydrogencarbonate or sodium hydroxide, then to a drying with magnesium sulfate anhydride or sodium sulfate anhydride, and then to filtration. Then, it is possible to use the resulting optically active imine solution containing a solvent of, for example, toluene in the first process.

In the first process, examples of a hemiacetal or hydrate of a perfluoroalkylaldehyde, which is represented by the general formula [3], are fluoral methylhemiacetal, fluoral ethylhemiacetal, fluoral n-propylhemiacetal, fluoral i-propylhemiacetal, fluoral hydrate, pentafluoropropionaldehyde ethylhemiacetal, pentafluoropropionaldehyde hydrate, n-heptabutylaldehyde ethylhemiacetal, and n-heptabutylaldehyde hydrate. In the first process, the hemiacetal or hydrate is reacted in an amount equimolar with the optically active imine. Therefore, it suffices to use the hemiacetal or hydrate in an amount of 1 mol or greater, preferably 1–10 moles, more preferably 1–5 moles, per mol of the optically active imine.

The condensation of the first process may be conducted with or without solvent. Examples of the solvent are (1) aliphatic hydrocarbons such as n-pentane, n-hexane, c-hexane, and n-heptane; (2) aromatic hydrocarbons such as benzene, toluene, ethylbenzene, and xylene; (3) halogenated hydrocarbons such as methylene chloride, chloroform, and 1,2-dichloroethane; (4) ethers such as diethyl ether, methyltert-butyl ether, tetrahydrofuran, and 1,4-dioxane; (5) esters such as ethyl acetate and n-butyl acetate; and (6) nitriles such as acetonitrile and propionitrile. Of these, it is preferable to use n-hexane, benzene, toluene, methylene chloride, 1,2-dichloroethane, tetrahydrofuran and acetonitrile. It is more preferable to use n-hexane and toluene. It is possible to use a single solvent or a mixture of at least two of these. The amount of the solvent used in the first process is not particularly limited. The condensation of the first process can be conducted at a temperature of −40 to 250° C., preferably of −20 to 100° C., more preferably of −10 to 80° C.

In the first process, the hydrolysis is conducted under an acid condition after the condensation, in order to turn an intermediate into the optically active perfluoroallkylcarbinol derivative represented by the general formula [1]. This intermediate is an oxetane represented by the general formula [13], or an N, O-acetal represented by the general formula [14], or an imine represented by the general formula [15],

[13]

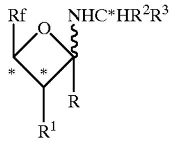

where R, $R^1$, a combination of R and $R^1$, Rf and the symbol * are defined as in the general formula [1], each of $R^2$ and $R^3$ is defined as in the general formula [2], and $R^2$ and $R^3$ are not the same substituted groups at the same time,

[14]

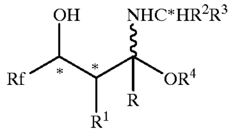

where R, $R^1$, a combination of R and $R^1$, Rf and the symbol * are defined as in the general formula [1], each of $R^2$ and $R^3$ is defined as in the general formula [2], $R^2$ and $R^3$ are not the same substituted groups at the same time, and $R^4$ is defined as in the general formula [3],

[15]

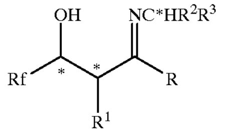

where R, $R^1$, a combination of R and $R^1$, Rf and the symbol * are defined as in the general formula [1], each of $R^2$ and $R^3$ is defined as in the, general formula [2], and $R^2$ and $R^3$ doe not become the same substituted groups at the same time.

In the hydrolysis of the first process, an acid is used for making an acid condition. Examples of this acid are organic acids such as p-toluenesulfonic acid and 10-camphorsulfonic acid, and inorganic acids such as hydrochloric acid, sulfuric acid and phosphoric acid. Of these, hydrochloric acid and sulfuric acid are preferable. In particular, hydrochloric acid is more preferable. The concentration of this acid can be adjusted to 0.1–12 N, preferably 0.2–6 N, more preferably 0.5–2 N. The amount of this acid used in the hydrolysis may be 0.1–20 moles, preferably 0.2–10 moles, more preferably 0.5–8 moles, per mol of the optically active imine. The temperature for conducting the hydrolysis is not particularly limited. It may be in the vicinity of room temperature. The hydrolysis becomes efficient under a heated condition. It is possible to get a sufficient reaction rate even under a cooled condition.

After the hydrolysis, it is possible to conduct a conventional post-treatment, thereby obtaining a crude product of the optically active perfluoroalkylcarbinol derivative. According to need, this crude product can be subjected to a purification such as the use of activated carbon, distillation, recrystallization, or column chromatography, thereby obtaining the optically active perfluoroalkylcarbinol derivative of high purity.

It is possible to collect and reuse a by-product of the hydrolysis, that is, the optically active primary amine represented by the general formula [12]. For example, it is possible to collect a crude optically active primary amine from an acid aqueous layer obtained by the post-treatment, by neutralization, extraction and/or the like. This crude optically active primary amine can be subjected to a purification such as the use of activated carbon, distillation, recrystallization, or column chromatography, thereby collecting the optically active primary amine of high purity. This product is not lowered in optical purity, and therefore it is possible to reuse it in the synthesis of the optically active imine.

The second process for increasing optical purity of an optically active 4,4,4-trifluoro-3-hydroxy-1-aryl-1-butanone derivative represented by the general formula [4] will be described in detail in accordance with the second aspect of the invention, as follows. It is possible to easily and efficiently increase optical purity of an optically active 4,4,4-trifluoro-3-hydroxy-1-aryl-1-butanone derivative represented by the general formula [4] in an industrial scale. According to need, the second process can be conducted by using a recrystallization solvent and/or by adding racemic seed crystals. It is possible to obtain the target product with a further increased optical purity by repeating the second process.

The target product obtained by the second process may be subjected to the after-mentioned Baeyer-Villiger oxidation, thereby obtaining an optically active 4,4,4-trifluoro-3-hydroxybutyric acid aryl ester derivative with high optical purity, represented by the general formula [5].

In the general formula [4] representing an optically active 4,4,4-trifluoro-3-hydroxy-1-aryl-1-butanone derivative used in the second process, X is a hydrogen or a substituent, that is, a $C_{1-6}$ alkyl, a $C_{1-6}$ alkoxy, or a halogen atom (F, Cl, Br or I). The position of this substituent is preferably ortho or para position, more preferably para position. Examples of the $C_{1-6}$ alkyl are straight-chain and branched lower alkyl groups (carbon atom number: 1–6) such as methyl, ethyl, n-propyl, i-propyl, n-butyl, i-butyl, sec-butyl, tert-butyl, n-pentyl, and n-hexyl. Examples of the $C_{1-6}$ alkoxy are straight-chain and branched lower alkoxy groups (carbon atom number: 1–6) such as methoxy, ethoxy, n-propoxy, i-propoxy, n-butoxy, i-butoxy, sec-butoxy, tert-butoxy, n-pentyloxy, and n-hexyloxy.

The process for producing the optically active 4,4,4-trifluoro-3-hydroxy-1-aryl-1-butanone derivative used in the second process is not particularly limited. For example, it may be the first process. As another example, it is possible to obtain this derivative by (a) reacting α-methoxystyrene derivative with a fluoral in the presence of an optically active binaphthol-titanium complex to obtain a product corresponding to that of Friedel-Crafts reaction; and then by (b) subjecting this product to an acid hydrolysis.

The second process (racemic crystal precipitation) is very effective for increasing especially the optically active 4,4,4-trifluoro-3-hydroxy-1-aryl-1-butanone derivative in optical purity, as explained in the following. As shown in the general formula [4], this derivative has in the same molecule hydroxyl and ketone groups each being capable of forming hydrogen bonding. It is evident from the X-ray crystal structure analysis of a racemic single crystal of this derivative that a hydrogen bonding is formed between the hydroxyl group of the S-form of this derivative and the ketone group of the R-form of this derivative, that another hydrogen bonding is formed between the hydroxyl group of the R-form and the ketone group of the S-form, and that the aryl groups of the derivative take a laminate structure form. Therefore, this derivative used in the second process is a compound of which racemic crystals are easily and selectively precipitated.

In order to conduct the racemic crystal precipitation in the second process, a recrystallization solvent may or may not be used, depending on the optical purity of the raw material, the target optical purity after the optical purification, recovery and the like. Furthermore, it becomes possible to smoothly and efficiently precipitate the racemic crystals by adding racemic seed crystals. The derivative to be purified by the second process may contain an excessive amount of either one of R- and S-forms and has an optical purity preferably of not less than 5% ee.

The recrystallization solvent used in the second process is not particularly limited so long as it does not react with the derivative to be purified. A suitable recrystallization solvent can be selected depending on the optical purity of the raw material, the target optical purity after the optical purification, recovery and the like. Examples of the recrystallization solvent are (1) aliphatic hydrocarbons such as n-pentane, n-hexane, c-hexane, and n-heptane; (2) aromatic hydrocarbons such as benzene, toluene, ethylbenzene, and xylene; (3) halogenated hydrocarbons such as methylene chloride, chloroform, and 1,2-dichloroethane; (4) ethers such as diethyl ether, methyl-tert-butyl ether, tetrahydrofuran, and 1,4-dioxane; (5) esters such as ethyl acetate and n-butyl acetate; and (6) ketones such as acetone and methyl ethyl ketone. Of these, n-hexane, toluene, ethyl acetate and acetone are preferable. In particular, n-hexane is more preferable. It is possible to use a single solvent or a mixture of at least two of these.

The second process can be conducted by dissolving the optically active 4,4,4-trifluoro-3-hydroxy-1-aryl-1-butanone derivative in a recrystallization solvent, then by precipitating only racemic crystals of this derivative to conduct a recrystallization, and then by removing the racemic crystals from the solution through filtration or the like. The temperature of this recrystallization can suitably be selected depending on the solvent's boiling point and freezing point. In fact, it is possible to dissolve the derivative in the recrystallization solvent at a temperature between about room temperature (25° C.) and about the boiling point of the recrystallization solvent. Furthermore, it is possible to precipitate the racemic crystals at a temperature of −40 to 80° C. For example, if n-hexane (freezing point: −94° C.; boiling point: 69° C.) is used as the recrystallization solvent, it is preferable to dissolve the derivative at a temperature of 30–69° C. and to precipitate the racemic crystals at a temperature of −20–65° C. The amount of the recrystallization solvent is not particularly limited, so long as the derivative is completely dissolved, and can be decided depending on the optical purity of the raw material, the target optical purity after the optical purification, recovery and the like. The amount of the racemic seed crystals is preferably 1/10,000 to 1/10 parts by weight, more preferably 1/1,000 to 1/20 parts by weight, per one part by weight of the derivative.

Optical purity of the optically active 4,4,4-trifluoro-3-hydroxy-1-aryl-1-butanone derivative can be determined in terms of enantiomeric excess (% ee) by measuring the peak area of each of the R- and S-forms in the chiral HPLC analysis (DAICEL OD-H, n-hexane:i-propanol=95:5, 254 nm).

The third process for increasing optical purity of an optically active 4,4,4-trifluoro-3-hydroxy-1-aryl-1butanone derivative represented by the general formula [4] will be described in detail in accordance with the third aspect of the invention, as follows. This third process comprises recrystallizing this derivative. It is possible to remarkably improve optical purity of the derivative by this recrystallization. In particular, it becomes possible to efficiently conduct the recrystallization in case that the derivative prior to the third process has an optical purity of 90% ee or greater and that seed crystals having an optical purity of 99% ee or greater are used in the recrystallization. In other words, if the derivative has an optical purity less than 90% ee, it is preferable to firstly conduct the second process for increasing the optical purity to 90% ee or greater and then conduct the third process for further increasing the optical purity.

As mentioned above, the racemic crystal of the derivative to be purified by the second process has two hydrogen bondings between the R- and S-forms and therefore becomes a stable crystal. In contrast, the optically pure crystal of the derivative, which consists of only R- or S-form, has only one hydrogen bonding between hydroxyl groups of two molecules of the R- or S-form and therefore it is crystal less stable than the racemic crystal. Thus, as shown in Table 1, the racemic crystal is higher in melting point than the optically pure crystal. When it is tried to increase optical purity of an optically active 4,4,4-trifluoro-3-hydroxy-1-aryl-1-butanone derivative by recrystallization, racemic crystals of this derivative are selectively precipitated. Therefore, it may be difficult to obtain the optical-purity-increased derivative in the form of crystals.

TABLE 1

| General Formula [4] of Derivative | Melting Point of Racemic Crystal (° C.) | Melting Point of Optically Pure Crystal (° C.) |
|---|---|---|
| 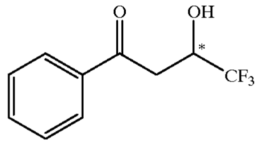 | 80–81 | 49 |
| 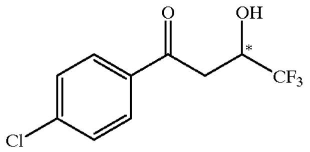 | 107–108 | 63–64 |

For example, the results of the after-mentioned Referential Example 3-1 show that optical purity of crystals precipitated by recrystallization from a solution (solvent: n-hexane) of (R)-4,4,4-trifluoro-3-hydroxy-1-phenyl-1-butanone (optical purity: 49.5% ee) has decreased from 49.5% ee to 25.1% ee (R), and in contrast optical purity of the mother liquor after the recrystallization has increased from 49.5% ee to 94.0% ee (R). It is common to precipitate crystals having a higher optical purity through recrystallization, but it may be difficult to directly use such recrystallization technique for increasing optical purity of an optically active 4,4,4-trifluoro-3-hydroxy-1-aryl-1-butanone derivative of the invention, as shown in Referential Example 3-1. The inventors, however, have unexpectedly found that, if such butanone derivative is previously adjusted to having an optical purity of 90% ee or greater, optical-purity-increased crystals, not racemic crystals, are precipitated by recrystallization. Furthermore, we have unexpectedly found that such crystals are smoothly and efficiently precipitated by using in recrystallization seed crystals having an optical purity of 99% ee or greater. Thus, according to the invention, it is preferable to sequentially conduct the second process for increasing optical purity of the derivative to 90% ee or greater and then the third process for further increasing optical purity of the derivative obtained by the second process. Alternatively, it is optional to omit the second process, if the derivative with an optical purity of 90% ee or greater is used in the third process.

An optically active 4,4,4-trifluoro-3-hydroxy-1-aryl-1-butanone derivative used in the third process may be the same as that used in the second process, except that it is preferable to adjust the derivative used in the third process to having an optical purity of 90% ee or greater. Therefore, the above-mentioned descriptions relating to the derivative used in the second process are not repeated herein.

A recrystallization solvent used in the third process is not particularly limited so long as it does not react with the derivative to be purified. A suitable recrystallization solvent can be selected depending on the optical purity of the raw material, the target optical purity after the optical purification, recovery and the like. Examples of the recrystallization solvent are (1) aliphatic hydrocarbons such as n-pentane, n-hexane, c-hexane, and n-heptane; (2) aromatic hydrocarbons such as benzene, toluene, ethylbenzene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and 1,4-dioxane; (5) ketones such as acetone, methyl ethyl ketone, and methyl isobutyl ketone; (6) esters such as ethyl acetate and n-butyl acetate; (7) nitrites such as acetonitrile and propionitrile; (8) alcohols such as methanol, ethanol, n-propanol, i-propanol, and n-butanol; and (9) water. Of these, preferable examples are n-hexane, n-heptane, toluene, methylene chloride, t-butyl methyl ether, acetone, ethyl acetate, acetonitrile, methanol, ethanol and i-propanol. In particular, more preferable examples are n-hexane, n-heptane, toluene, t-butyl methyl ether, acetone, ethyl acetate, and i-propanol. It is possible to use a single solvent or a mixture of at least two of these.

As long as it can completely or partially dissolve the optically active 4,4,4-trifluoro-3-hydroxy-1-aryl-1-butanone derivative upon heating, the amount of the recrystallization solvent used in the third process is not particularly limited and can be decided depending on the optical purity of the raw material, the target optical purity after the optical purification, recovery and the like. It suffices to use the recrystallization solvent in an amount of 1 part by volume (e.g., 1 ml) or greater, preferably 1–200 parts by volume, more preferably 1–100 parts by volume, relative to 1 part by weight (e.g., 1 g) of the derivative to be purified by the third process.

Similar to the second process, the temperature of the recrystallization of the third process can suitably be selected depending on the solvent's boiling point and freezing point. In fact, it is possible to dissolve the derivative in the recrystallization solvent at a temperature between about room temperature (25° C.) and about the boiling point of the recrystallization solvent. Furthermore, it is possible to precipitate optical-purity-increased crystals at a temperature of −40 to 80° C. For example, if n-hexane is used as the recrystallization solvent, it is preferable to dissolve the derivative at a temperature of 30–69° C. and to precipitate optical-purity-increased crystals at a temperature of −20–65° C.

The seed crystals used in the third process are in an amount of preferably 1/10,000 to 1/10 parts by weight, more preferably 1/5,000 to 1/20 parts by weight, per one part by weight of the derivative to be purified by the third process.

In the third process, the solution may be allowed to stand still or stirred to precipitate crystals. The precipitated crystals are recovered by filtration or the like, thereby obtaining an optically active 4,4,4-trifluoro-3-hydroxy-1-aryl-1-butanone derivative with high optical purity. Furthermore, it becomes possible to further increase optical purity of this derivative by repeating the recrystallization.

The fourth process for producing an optically active 4,4,4-trifluoro-3-hydroxybutyric acid aryl ester derivative represented by the general formula [5] will be described in detail in accordance with the fourth aspect of the invention, as follows. The fifth process for producing an optically inactive 4,4,4-trifluoro-3-hydroxybutyric acid aryl ester derivative represented by the general formula [6] is the same as the fourth process except in that an optically inactive 4, 4,4-trifluoro-3-hydroxy-1-aryl-1-butanone derivative represented by the general formula [7] is oxidized. Therefore, the following descriptions of the fourth process are applicable to the fifth process and therefore are not repeated hereinafter.

As stated above, the fourth process comprises oxidizing an optically active 4,4,4-trifluoro-3-hydroxy-1-aryl-1-butanone derivative represented by the general formula [4], thereby achieving Baeyer-Villiger oxidation and producing the aryl ester derivative. In other words, it is possible to easily and efficiently produce the aryl ester in an industrial scale without lowering optical purity by subjecting the butanone derivative to Baeyer-Villiger oxidation.

The butanone derivative used in the fourth process may be the same as that used in the second process. Therefore, the above-mentioned descriptions relating to the butanone derivative used in the second process are not repeated herein. If it is, however, necessary to produce the aryl ester derivative with very high optical purity, it is preferable to sequentially conduct the second, third and fourth processes. In other words, it is preferable to use in the fourth process the butanone derivative obtained by the third process.

In the fourth process, the Breyer-Villiger oxidation can be conducted by using an oxidizing agent. Examples of such oxidizing agent are metachloroperbenzoic acid (m-CPBA), peracetic acid (including a mixture of acetic acid and hydrogen peroxide aqueous solution and a mixture of acetic anhydride and hydrogen peroxide aqueous solution), trifluoroperacetic acid (including a mixture of trifluoroacetic acid and hydrogen peroxide aqueous solution and a mixture of trifluoroacetic anhydride and hydrogen peroxide aqueous solution), and peroxophosphoric acid. Of these, preferable examples are trifluoroperacetic acid (including a mixture of trifluoroacetic acid and hydrogen peroxide aqueous solution and a mixture of trifluoroacetic anhydride and hydrogen peroxide aqueous solution) and peroxophosphoric acid. In particular, peroxophosphoric acid is inexpensive. Therefore, it becomes possible to produce the aryl ester derivative with a reduced cost. Peroxophosphoric acid can easily be prepared from phosphorus pentoxide and hydrogen peroxide aqueous solution, in acetonitrile (see Chem. Ber., 48, 1162 (1910); J. Am. Chem. Soc., 59, 555 (1937); and J. Org. Chem, 43, 2417 (1978)). The concentration of this hydrogen peroxide aqueous solution in acetonitrile is not particularly limited, since phosphorus pentoxide serves as a dehydrating agent.

In the Baeyer-Villiger oxidation, it suffices to use the oxidizing agent in an amount of 1 mole or greater, preferably 1–20 moles, more preferably 1–10 moles, per mol of the optically active 4,4,4-trifluoro-3-hydroxy-1-aryl-1-butanone derivative represented by the general formula [4].

It is optional to use a Brönsted acid in the Baeyer-Villiger oxidation in order to accelerate the reaction. Examples of such Brönsted acid are (1) organic acids such as formic acid, acetic acid, propionic acid, trifluoroacetic acid, trichloroacetic acid, methanesulfonic acid, p-toluenesulfonic acid, 10-camphorsulfonic acid and trifluoromethanesulfonic acid; and (2) inorganic acids such as sulfuric acid, phosphoric acid, perchloric acid and periodic acid. Of these, sulfuric acid is preferable. The Brönsted acid in the Baeyer-Villiger oxidation may be in a catalytic amount, preferably 0.01–20 moles, more preferably 0.05–10 moles, per mol of the optically active 4,4,4-trifluoro-3-hydroxy-1-aryl-1-butanone derivative represented by the general formula [4]. It is needless to say that the addition of the Brönsted acid can be omitted if the Baeyer-Villiger oxidation proceeds with a sufficiently high reaction rate.

The Baeyer-Villiger oxidation can be conducted by using a reaction solvent. Examples of the reaction solvent may be (1) aliphatic hydrocarbons such as n-pentane, n-hexane, c-hexane and n-heptane; (2) aromatic hydrocarbons such as benzene, toluene and ethylbenzene and xylene; (3) halogenated hydrocarbons such as methylene chloride, chloroform and 1,2-dichloroethane; (4) esters such as ethyl acetate and n-butyl acetate; (5) alcohols such as methanol, ethanol and n-propanol; (6) carboxylic acids such as acetic acid, propionic acid, trifluoroacetic acid and trichloroacetic acid; (7) carboxylic anhydrides such as acetic anhydride, propionic anhydride, trifluoroacetic anhydride and trichloroacetic anhydride; and (9) water. Of these, preferable examples are methylene chloride, 1,2-dichloroethane, acetic acid, trifluoroacetic acid, acetic anhydride and trifluoroacetic anhydride. More preferable examples are methylene chloride, trifluoroacetic acid and trifluoroacetic anhydride. In case that peroxophosphoric acid is used as an oxidizing agent, preferable examples of a reaction solvent used in the Baeyer-Villiger oxidation are (1) nitrites such as acetonitrile, propionitrile, butyronitrile, isobutyronitrile and benzonitrile; (2) aliphatic hydrocarbons such as n-pentane, n-hexane, c-hexane and n-heptane; (3) aromatic hydrocarbons such as benzene, toluene and ethylbenzene and xylene; (4) esters such as ethyl acetate, n-propyl acetate and n-butyl acetate; (5) ethers such as diethyl ether, methyl t-butyl ether, tetrahydrofuran and 1,4-dioxane; (6) alcohols such as methanol, ethanol, n-propanol and i-propanol; (7) carboxylic acids such as acetic acid, propionic acid and butyric acid; (8) carboxylic anhydrides such as acetic anhydride, propionic anhydride and butyric anhydride; and (9) water. Of these preferable examples, more preferable examples are acetonitrile, propionitrile, n-heptane, toluene, ethyl acetate, tetrahydrofuran, methanol, acetic acid, acetic anhydride and water. In particular, still more preferable examples are acetonitrile and propionitrile. The reaction solvent may be a single compound or a mixture of at least two of these compounds. In fact, it is possible to prepare peroxophosphoric acid in acetonitrile. Therefore, to the peroxophosphoric acid solution it is possible to add an optically active 4,4,4-trifluoro-3-hydroxy-1-aryl-1-butanone derivative represented by the general formula [4] neat or a mixture of this derivative and a reaction solvent.

The Baeyer-Villiger oxidation can proceed easily at about room temperature. It can proceed efficiently under heating. Even under cooling (e.g., about 0° C.), it can proceed with a sufficient reaction rate.

After the Baeyer-Villiger oxidation, it is possible to conduct a conventional post-treatment, thereby obtaining a crude product of an optically active 4,4,4-trifluoro-3-hydroxybutyric acid aryl ester derivative represented by the general formula [5]. For example, peroxophosphoric acid remaining after the Baeyer-Villiger oxidation can be decomposed by a reducing agent such as sodium sulfite or sodium thiosulfate. After that, it is possible to conduct a conventional post-treatment, thereby obtaining the crude product. According to need, this crude product can be subjected to a purification such as activated carbon treatment, distillation, recrystallization, or column chromatography, thereby obtaining the optically active aryl ester derivative of high purity.

The sixth process for increasing optical purity of an optically active 4,4,4-trifluoro-3-hydroxybutanoic aryl ester derivative represented by the general formula [5] will be described in detail in accordance with the fifth aspect of the invention, as follows. As stated above, Helvetica Chimica Acta, 67, 1843, 1984 discloses that selective precipitation of racemic crystals occurs in recrystallization of 4,4,4-trifluoro-3-hydroxybutyric acid ethyl ester, and thereby optical purity of the mother liquor is improved. The inventors, however, have unexpectedly found a totally different phenomenon, in which precipitated crystals are remarkably increased in optical purity by recrystallization, by using the optically active 4,4,4-trifluoro-3-hydroxybutanoic aryl ester derivative. In fact, this aryl ester derivative has an aryl group, and in contrast the above butyric acid ethyl ester has an alkyl group (ethyl). This difference unexpectedly brings about the above-mentioned totally opposite phenomena.

In the sixth process, the aryl group of the optically active 4,4,4-trifluoro-3-hydroxybutanoic aryl ester derivative represented by the general formula [5] may be the same as that of the optically active 4,4,4-trifluoro-3-hydroxy-1-aryl-1-butanone derivative represented by the general formula [4]. Therefore, the above-mentioned detailed explanation of the aryl group of the butanone derivative is applicable to the aryl ester derivative and therefore is not repeated herein. As stated above, the symbol * in the general formula [5] represents an asymmetric carbon. The optically active aryl ester derivative used in the sixth process is R-form or S-form in stereochemistry and has an optical purity preferably of 50% ee or greater. The process for producing this aryl ester derivative is not particularly limited and may be the fourth process of the invention.

A recrystallization solvent used in the sixth process is not particularly limited so long as it does not react with the aryl ester derivative to be purified. A suitable recrystallization solvent can be selected depending on the optical purity of the raw material, the target optical purity after the optical purification, recovery and the like. Examples, preferable examples and more preferable examples of the recrystallization solvent are the same as those of the third process and therefore are not recited herein. It is also possible to use a single solvent or a mixture of at least two solvents. As long as it can completely or partially dissolve the optically active 4,4,4-trifluoro-3-hydroxybutyric acid aryl ester derivative upon heating, the amount of the recrystallization solvent used in the sixth process is not particularly limited and can be selected depending on the optical purity of the raw material, the target optical purity after the optical purification, recovery and the like. It suffices to use the recrystallization solvent in an amount of 1 part by volume (e.g., 1 ml) or greater, preferably 1–100 parts by volume, more preferably 1–50 parts by volume, relative to one part by weight (e.g., 1 g) of the aryl ester derivative to be purified by the sixth process.

All of the above descriptions of the recrystallization temperature of the third process are applicable to those of the sixth process and therefore are not repeated herein.

In the sixth process, it is possible to smoothly and efficiently precipitate crystals of the aryl ester derivative by adding seed crystals of a high optical purity. Similar to the third process, the seed crystals used in the sixth process are in an amount of preferably 1/10,000 to 1/10 parts by weight, more preferably 1/5,000 to 1/20 parts by weight, per one part by weight of the derivative to be purified by the sixth process.

In the sixth process, the solution may be allowed to stand still or stirred to precipitate crystals. The precipitated crystals are recovered by filtration or the like, thereby obtaining an optically active 4,4,4-trifluoro-3-hydroxybutyric acid aryl ester derivative with high optical purity. Furthermore, it becomes possible to further increase optical purity of this derivative by repeating the recrystallization.

The seventh process for producing an optically active 4,4,4-trifluoro-1,3-butanediol represented by the general formula [8] will be described in detail in accordance with the sixth aspect of the invention, as follows. This butanediol can be produced easily and efficiently in an industrial scale by the seventh process.

As mentioned above, there is a conventional process in which (R)-4,4,4-trifluoro-3-hydroxybutyric acid ethyl ester is reduced by sodium borohydride, thereby obtaining (R)-4,4,4-trifluoro-1,3-butanediol (see U.S. Pat. No. 5,716,841). In contrast with this, the inventors have unexpectedly found that an optically active 4,4,4-trifluoro-3-hydroxybutyric acid aryl ester derivative represented by the general formula [5] can also be reduced by a hydride, thereby obtaining the butanediol. In view of the fact that alkyl esters are very different from aryl esters in reactivity in general organic syntheses, it was not known if the aryl ester derivative can be reduced under a reaction condition disclosed in U.S. Pat. No. 5,716,841.

The aryl ester derivative used in the seventh process may be the same as that of the sixth process. Therefore, the above-mentioned detailed explanation of the aryl ester derivative used in the sixth process is applicable to that used in the seventh process and therefore is not repeated herein.

The hydride used as a reducing agent in the seventh process is not particularly limited. Its examples are (1) aluminum hydrides such as $(i\text{-}Bu)_2AlH$, $(i\text{-}Bu)_3Al$, $[2,6\text{-}(t\text{-}Bu)_2\text{-}4\text{-}Me.Ph]Al(i\text{-}Bu)_2$, $LiAlH_4$, $LiAlH(OMe)_3$, $LiAlH(O\text{-}t\text{-}Bu)_3$, and $NaAH_3(OCH_2CH_2OCH_3)_2$; (2) borohydrides such as diborane, $BH_3$.THF, $BH_3.SMe_2$, $BH_3.NMe_3$, 9-BBN, $NaBH_4$, $NaBH_4\text{-}CeCl_3$, $LiBH_4$, $Zn(BH_4)_2$, $Ca(BH_4)_2$, $Et_4NBH_4$, $Lin\text{-}BuBH_3$, $NaBH(OMe)_3$, $NaBH(OAc)_3$, $Me_4NBH(OAc)_3$, $(n\text{-}Bu)_4NBH(OAc)_3$, $NaBH_3CN$, $(n\text{-}Bu)_4NBH_3CN$, $Li(s\text{-}Bu)_3BH$, $K(s\text{-}Bu)_3BH$, $LiSia_3BH$, $KSia_3BH$, $LiEt_3BH$, $KPh_3BH$, $(Ph_3P)_2CuBH_4$, $ThxBH_2$, $Sia_2BH$, catecholborane, $IpcBH_2$, and $Ipc_2BH$; and (3) silicon hydrides such as $Et_3SiH$, $PhMe_2SiH$, $Ph_2SiH_2$, and $PhSiH_3\text{-}Mo(CO)_6$. Of these, preferable examples are $LiAlH_4$, diborane, $BH_3$.THF, $NaBH_4$, and $LiBH_4$. In particular, $NaBH_4$ is more preferable. It is possible to use a combination of at least one of these hydrides and at least one of various inorganic salts. In the seventh process, it suffices to use the hydride in an amount of 1 mol or greater, preferably 1–10 moles, more preferably 1–5 moles, per mol of the optically active 4,4,4-trifluoro-3-hydroxybutyric acid aryl ester derivative.

A reaction solvent used in the seventh process is not particularly limited. Its examples are (1) aliphatic hydrocarbons such as n-pentane, n-hexane, c-hexane, and n-heptane; (2) aromatic hydrocarbons such as benzene, toluene, ethylbenzene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and 1,4-dioxane; (5) nitriles such as acetonitrile and propionitrile; (6) alcohols such as methanol, ethanol, n-propanol, i-propanol, and n-butanol; and (7) water. Of these, preferable examples are diethyl ether, tetrahydrofuran, t-butyl methyl ether, and 1,4-dioxane. In particular, tetrahydrofuran is more preferable. It is possible to use a single solvent or a mixture of at least two of these. In the seventh process, it suffices to use a reaction solvent in an amount of 0.1–100 parts by volume (e.g., 0.1–100 ml), preferably 0.5–50 parts by volume, more preferably 1–30 parts by volume, relative to one part by weight (e.g., 1 g) of the optically active 4,4,4-trifluoro-3-hydroxybutyric acid aryl ester.

It suffices to conduct the seventh process (reduction) at a temperature of −80–150° C., preferably 40–125° C., more preferably −20–100° C. The reaction time of the seventh process depends on reaction conditions, but may be 0.1–24 hr. The seventh process can be conducted in an open system or in an atmosphere of an inert gas (e.g., nitrogen or argon).

In the seventh process, the reaction can be terminated by adding water or an acid aqueous solution such as saturated ammonium chloride aqueous solution or diluted hydrochloric acid. Then, it is possible to efficiently break oxygen-boron bonding of an optically active 4,4,4-trifluoro-1,3-butanediol-boron complex remaining after the reaction, by heating. Then, it is possible to conduct a conventional post-treatment, thereby collecting a crude product of a high-optical-purity 4,4,4-trifluoro-1,3-butanediol with good yield. It is particularly effective to add water to the reaction liquid after the reaction and then conduct stirring for 2 hr under a tetrahydrofuran-water reflux, thereby collecting the crude product. This crude product contains phenols (by-products) in an equimolar amount, and therefore it is necessary to conduct a separation to remove these phenols therefrom. Exemplary steps for the separation are activated carbon treatment, distillation, recrystallization, column chromatography, washing with an basic aqueous solution, and adsorption to ion exchange resin. Of these, distillation is preferable. The way of the separation can be selected depending on the types of the phenols. The separation can be conducted by a single step or a combination of at least two of these steps.

The eighth process for producing an optically active 4,4,4-trifluoro-3-hydroxybutyric acid alkyl ester derivative represented by the general formula [9] will be described in detail in accordance with the seventh aspect of the invention, as follows. It is possible by the eighth process to easily and efficiently produce such optically active alkyl ester derivative in an industrial scale without lowering optical purity. The ninth process for producing an optically inactive 4,4,4-trifluoro-3-hydroxybutyric acid alkyl ester derivative represented by the general formula [10] is the same as the eighth process except in that an optically inactive 4,4,4-trifluoro-3-hydroxy-butyric acid aryl ester derivative represented by the general formula [6] is reacted with the lower alcohol. Therefore, the following descriptions of the eighth process are applicable to the ninth process and therefore are not repeated hereinafter.

As stated above, the optically active 4,4,4-trifluoro-3-hydroxybutyric acid aryl ester derivative represented by the general formula [5] used in the eighth process can be obtained by the fourth process. In the eighth process, the optically active aryl ester derivative is reacted under an acid condition with a lower alcohol represented by the general formula ROH where R is a $C_{1-6}$ alkyl, thereby achieving an ester exchange and producing the optically active alkyl ester derivative.

Examples of the lower alcohol used in the eighth process are methanol, ethanol, n-propanol, i-propanol, n-butanol, i-butanol, sec-butanol, tert-butanol, n-pentanol, and n-hexanol. Of these, methanol and ethanol are particularly preferable. In the eighth process, the lower alcohol to be reacted with the aryl ester derivative may be in an amount of 1 mole or greater, preferably 1–100 moles, per mol of the aryl ester derivative. It is more preferable to use the lower alcohol as a reaction solvent in an amount of 100 moles or greater.

It is possible to use an acid catalyst in the eighth process. Examples of this acid catalyst are organic acids such as p-toluenesulfonic acid and 10-camphorsulfonic acid, and inorganic acids such as hydrochloric acid, sulfuric acid and phosphoric acid. Of these, p-toluenesulfonic acid is particularly preferable. It suffices to use this acid catalyst in a catalytic amount, preferably 0.001–1 mole, more preferably 0.01–0.5 moles, per mole of the aryl ester derivative.

In the eighth process, it is possible to use a solvent other than the lower alcohol. Examples of such solvent are (1) aliphatic hydrocarbons such as n-pentane, n-hexane, c-hexane, and n-heptane; (2) aromatic hydrocarbons such as benzene, toluene, ethylbenzene, and xylene; (3) halogenated hydrocarbons such as methylene chloride, chloroform, and 1,2-dichloroethane; (4) ethers such as diethyl ether, methyl-tert-butyl ether, tetrahydrofuran, and 1,4-dioxane; and (5) nitrites such as acetonitrile and propionitrile. Of these, n-heptane, toluene and 1,2-dichloroethane are preferable. In particular, toluene is more preferable. It is possible to use a single solvent or a mixture of at least two of these solvents.

In the eighth process, it is possible to conduct the reaction at a temperature of −30–250° C., preferably 0–200° C., more preferably 20–150° C. After the reaction, it is possible to conduct a conventional post-treatment, thereby obtaining a crude product. According to need, this crude product can be subjected to a purification such as activated carbon treatment, distillation, recrystallization, or column chromatography, thereby obtaining the optically active alkyl ester derivative with high purity.

The following nonlimitative examples including referential examples are illustrative of the present invention. The following Examples 1-1 to 1-32 including Examples 1-7a and 1-7d are illustrative of the first process.

[1] Production of Optically Active Imine

EXAMPLE 1-1

At first, as shown in Table 2, p-toluenesulfonic acid monohydrate (0.5 mmol) was added to a toluene solution (150 ml) containing acetophenone (1a, 50 mmol) as a ketone and (R)-1-phenylethylamine ((R)-2a, 100 mmol) as an optically active primary amine, followed by heating under reflux for 24 hr and by removing water (formed as a by-product) with a Dean-Stark tube during the reaction, in order to conduct the following reaction.

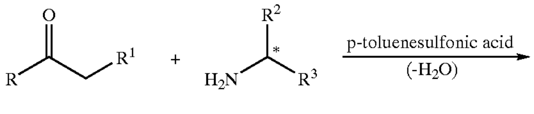

[11] [12]

-continued

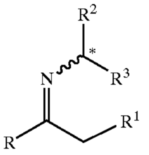

[2]

Then, the reaction liquid after the reaction was washed with a saturated sodium hydrogencarbonate aqueous solution, followed by drying with sodium sulfate anhydride, then filtration, then concentration, and then vacuum drying, thereby obtaining a crude product. Then, this crude product was subjected to a vacuum distillation (143° C./6 mmHg), thereby obtaining an optically active imine, (R)-N-(1-phenylethylidene)-1-phenylethylamine ((R)-3aa, 39 mmol, 78%), as shown in Table 2. In Table 2, R, $R^1$, $R^2$, and $R^3$ of the compound [2] are defined as in the compounds [11] and [12].

TABLE 2

| | Comp. [11] (50 mmol) | Cop. [12] (100 mmol) | Solvent | p-TsOH* (mol %) | Time (hr) | Comp. [2] | Yield (%) |
|---|---|---|---|---|---|---|---|
| Ex. 1-1 | R: phenyl $R^1$: H 1a | $R^2$: methyl $R^3$: phenyl (R)-2a | toluene | 1 | 24 | ditto for R, $R^1$, $R^2$, & $R^3$ (R)-3aa | 78 |
| Ex. 1-3 | R: phenyl $R^1$: H 1a | $R^2$: methyl $R^3$: phenyl (S)-2a | " | 1 | 24 | ditto for R, $R^1$, $R^2$, & $R^3$ (S)-3aa | 80 |
| Ex. 1-2 | R: phenyl $R^1$: H 1a | $R^2$: methyl $R^3$: 2'-naphthyl (R)-2b | " | 1 | 24 | ditto for R, $R^1$, $R^2$, & $R^3$ (R)-3ab | 81 |
| Ex. 1-4 | R: phenyl $R^1$: H 1a | $R^2$: methyl $R^3$: cyclohexyl (R)-2c | " | 1 | 24 | ditto for R, $R^1$, $R^2$, & $R^3$ (R)-3ac | 77 |
| Ex. 1-5 | R: phenyl $R^1$: H 1a | $R^2$: methoxy-carbonyl $R^3$: phenyl (S)-2d | " | 1 | 24 | ditto for R, $R^1$, $R^2$, & $R^3$ (S)-3ad | 84 |
| Ex. 1-6 | R: phenyl $R^1$: H 1a | $R^2$: methoxy-carbonyl $R^3$: isopropyl (S)-2e | " | 1 | 24 | ditto for R, $R^1$, $R^2$, & $R^3$ (S)-3ae | 76 |
| Ex. 1-7 | R: phenyl $R^1$: H 1a | $R^2$: hydroxy-methyl $R^3$: phenyl (S)-2f | " | 1 | 24 | ditto for R, $R^1$, $R^2$, & $R^3$ (S)-3af | 78 |

*% by mol of p-toluenesulfonic acid, based on the number of moles of the compound [11]

EXAMPLE 1-2

Example 1-1 was repeated except in that (R)-1-2'-naphthylethylamine ((R)-2b, 100 mmol) was used as an optically active primary amine, thereby obtaining an optically active imine, (R)-N-(1-phenylethylidene)-1-2'-naphthylethylamine ((R)-3ab, 40.5 mmol, 81%), as shown in Table 2.

EXAMPLES 1-3–1-7

In each of these examples, Example 1-1 was repeated except in that the compound [12] was changed, as shown in Table 2.

EXAMPLE 1-7a

At first, zinc chloride (0.14 g, 1 mmol) was added to a toluene solution (100 ml) containing 12.0 g (100 mmol) of acetophenone (1a) as a ketone and 13.3 g (110 mmol) of (S)-1-phenylethylamine ((S)-2a) as an optically active primary amine, followed by heating under reflux for 20 hr and by removing water (formed as a by-product) with a Dean-Stark tube during the reaction. Then, the reaction liquid after the reaction was washed with a 1N NaOH, followed by washing with 1N ammonium chloride aqueous solution, then drying with sodium sulfate anhydride, then filtration, then concentration, and then drying under vacuum, thereby obtaining 22.5 g of (S)-N-(phenylethylidene)-1-phenylethylamine ((S)-3aa, purity: 99%, yield: 100%).

EXAMPLE 1-7b

At first, zinc chloride (0.16 g, 1.1 mmol) was added to a toluene solution (100 ml) containing 16.6 g (107 mmol) of 4-chloroacetophenone (1b) as a ketone and 14.3 g (118 mmol) of (S)-1-phenylethylamine ((S)-2a) as an optically active primary amine. Then, the same steps as those of Example 1-7a were conducted, thereby obtaining 27.3 g of (S)-N-(1-phenylethylidene)-1-(4-chlorophenyl)-ethylamine ((S)-3ba, purity: 95%, yield: 94%).

EXAMPLE 1-7c

At first, 0.24 g (1.25 mmol) of p-toluenesulfonic acid monohydrate were added to a toluene solution (25 ml) containing 8.35 g (25 mmol) of 4-methylacetophenone (3c) as a ketone and 3.03 g (25 mmol) of (S)-1-phenylethylamine ((S)-2a) as an optically active primary amine, followed by heating under reflux for 24 hr and by removing water (formed as a by-product) with a Dean-Stark tube during the reaction, in order to conduct the reaction. Then, the reaction liquid after the reaction was washed with a saturated sodium hydrogencarbonate aqueous solution, followed by drying with sodium sulfate anhydride, then filtration, then concentration, and then vacuum drying, thereby obtaining as a crude product 5.66 g of (S)-N-(1-phenylethylidene)-1-(4-methylphenyl)-ethylamine ((S)-3ca, yield: 89%).

EXAMPLE 1-7d

In this example, Example 1-7c was repeated except that 3.35 g of 4-methylacetophenone of the toluene solution were replaced with 3.76 g (25 mmol) of 4-methoxyacetonphenone (3d), thereby obtaining as a crude product 5.83 g of (S)-N-(1-phenaylethylidene)-1-(4-methoxyphenyl)-ethylamine ((S)-3da, yield: 90%).

[2] Production of Optically Active Perfluoroalkylcarbinol Derivatives

EXAMPLE 1-8

As shown in Table 3, a n-hexane solution of 2 ml containing (R)-N-(1-phenylethylidene) 1-phenylethylamine represented by the formula [2] ((R)-3aa, 0.5 mmol) and fluoral-ethylhemiacetal represented by the formula [3] (4a, 0.5 mmol) was stirred for 7 hr at 18–19° C., followed by the addition of 12 ml of 1.5N HCl and then stirring for 1 hr at room temperature, thereby conducting the following reaction.

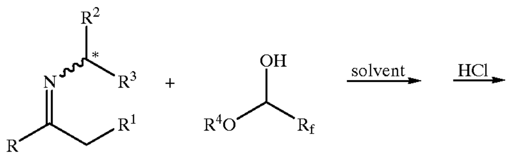

[2] [3]

-continued

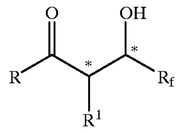

[1]

The reaction liquid after the reaction was extracted with ethyl acetate, followed by washing with saturated brine, then drying with sodium sulfate anhydride, then filtration, then concentration, and then vacuum drying, thereby obtaining a crude product. This crude product was purified by a column chromatography (ethyl acetate: n-hexane =1:5), thereby obtaining (S)-4,4,4-trifluoro-3-hydroxy-1-phenyl-1-butanone [1] ((S)-5aa, 0.31 mmol, 62%). Its optical purity was found to be 60% ee by a chiral HPLC (DAICEL OD, n-hexane:i-propanol=95:5, 254 nm).

EXAMPLE 1-9

At first, a n-hexane solution of 2 ml containing (R)-N-(1-phenylethylidene)-1-2'-naphthylethylamine ((R)-3ab, 0.5 mmol) and fluoral-ethylhemiacetal (4a, 0.5 mmol) was stirred for 168 hr at −2–0° C. Then, the same steps as those of Example 1-8 were repeated, thereby obtaining (S)-4,4,4-trifluoro-3-hydroxy-1-phenyl-1-butanone ((S)-5aa, 0.285 mmol, 57%). Its optical purity was found to be 81% ee by the same manner as that of Example 1-8.

EXAMPLES 1-10–1-26

In each of these examples, Example 1-8 was repeated except in that the reactants and the reaction conditions were changed, as shown in Table 3.

TABLE 3

| | Comp. [2] | Comp. [3] | [2]:[3] by mol* | Solvent | Temp. (° C.) | Time (hr) | Comp. [1] | Yield (%) | Optical Purity (% ee) |
|---|---|---|---|---|---|---|---|---|---|
| Ex. 1-10 | (R)-3aa | $R_1$: $CF_3$, $R^4$: ethyl, 4a | 1:1 | n-hexane | Reflux | 1 | R: phenyl, $R^1$: H, $R_1$: $CF_3$, (S)-5aa | 90 | 5 |
| Ex. 1-8 | (R)-3aa | " | 1:1 | n-hexane | 18–19 | 7 | " | 62 | 60 |
| Ex. 1-11 | (S)-3aa | " | 1:1 | n-hexane | 20–22 | 7 | R: phenyl, $R^1$: H, $R_1$: $CF_3$, (R)-5aa | 73 | 59 |
| Ex. 1-12 | (R)-3aa | " | 1:1 | Toluene | 19–20 | 7 | R: phenyl, $R^1$: H, $R_1$: $CF_3$, (S)-5aa | 64 | 55 |
| Ex. 1-13 | (R)-3aa | " | 1:1 | Terahydro-furan | 15–18 | 7 | " | 8 | 47 |
| Ex. 1-14 | (R)-3aa | " | 1:1 | Dichloro-methane | 15–18 | 7 | " | 61 | 43 |
| Ex. 1-15 | (R)-3aa | " | 1:1 | Acetonitrile | 20–22 | 7 | " | 56 | 44 |
| Ex. 1-16 | (R)-3ab | " | 1:1 | n-hexane | 18–19 | 7 | " | 66 | 71 |
| Ex. 1-17 | (R)-3ab | " | 1:1 | n-hexane | −3–1 | 7 | " | 19 | 77 |
| Ex. 1-18 | (R)-3ab | " | 1:1 | n-hexane | −1–1 | 24 | " | 27 | 79 |
| Ex. 1-19 | (R)-3ab | " | 1:1 | n-hexane | −1–0 | 72 | " | 39 | 80 |
| Ex. 1-9 | (R)-3ab | " | 1:1 | n-hexane | −2–0 | 16 | " | 57 | 81 |
| Ex. 1-20 | (R)-3ab | " | 1:2 | n-hexane | −2–0 | 24 | " | 44 | 77 |
| Ex. 1-21 | (R)-3ab | " | 1:3 | n-hexane | −1–1 | 24 | " | 67 | 75 |
| Ex. 1-22 | (R)-3ab | " | 1:5 | n-hexane | −1–1 | 24 | " | 71 | 73 |
| Ex. 1-23 | (R)-3ac | " | 1:1 | n-hexane | 20–22 | 7 | " | 92 | 25 |
| Ex. 1-24 | (S)-3ad | " | 1:1 | n-hexane | 18–21 | 7 | " | 79 | 3 |
| Ex. 1-25 | (S)-3ae | " | 1:1 | n-hexane | 19–20 | 7 | " | 55 | 23 |
| Ex. 1-26 | (S)-3af | " | 1:1 | n-hexane | 18–21 | 7 | " | 64 | 49 |

*the molar ratio of the compound [2] to the compound [3]

EXAMPLE 1-27

A n-hexane solution of 2 ml containing (S)-N-(1-phenylethylidene)-1-(4-chlorophenyl)-ethylamine ((S)-3ba, 0.5 mmol) and fluoral-ethylhemiacetal (4a, 0.5 mmol) was stirred for 17 hr at 18–19° C., followed by the addition of 2 ml of 1.5N HCl and then stirring for 1 hr at room temperature, thereby conducting the reaction. The reaction liquid after the reaction was extracted with ethyl acetate, followed by washing with saturated brine, then drying with sodium sulfate anhydride, then filtration, then concentration, and then vacuum drying, thereby obtaining as a crude product 95.1 mg of (R)-4,4,4-trifluoro-3-hydroxy-1-(4-chlorophenyl)-1-butanone ((R)-5ba, 0.32 mmol, yield: 64%). Its optical purity was found to be 58% ee by the same chiral HPLC as that of Example 1-8.

EXAMPLE 1-28

A n-hexane solution of 25 ml containing 5.66 g of (S)-N-(1-phenylethylidene)-1-(4-methylphenyl)-ethylamine ((S)-3ca) obtained in Example 1-7c and 27.5 mmol of fluoral-ethylhemiacetal (4a) was stirred for 17 hr at 18–19° C., followed by the addition of 25 ml of 1.5N HCl and then stirring for 1 hr at room temperature, thereby conducting the reaction. Then, the same steps as those of Example 1-27 were conducted, thereby obtaining as a crude product 5.88 g of (R)-4,4,4-trifluoro-3-hydroxy-1-(4-methylphenyl)-1-butanone ((R)-5ca, yield: 87%). Its optical purity was found to be 55% ee by the same chiral HPLC as that of Example 1-8.

EXAMPLE 1-29

A n-hexane solution of 25 ml containing 5.83 g of (S)-N-(1-phenylethylidene)-1-(4-methoxyphenyl)-ethylamine ((S)-3da) obtained in Example 1-7d and 27.5 mmol of fluoral-ethylhemiacetal (4a) was stirred for 15 hr at 18–19° C., followed by the addition of 25 ml of 1.5N HCl and then stirring for 1 hr at room temperature, thereby conducting the reaction. Then, the same steps as those of Example 1-27 were conducted, thereby obtaining as a crude product 5.83 g of (R)-4,4,4-trifluoro-3-hydroxy-1-(4-methoxyphenyl)-1-butanone ((R)-5da, yield: 72%). Its optical purity was found to be 33% ee by the same chiral HPLC as that of Example 1-8.

EXAMPLE 1-30

At first, 5.5 g (40 mmol) of zinc chloride were added to a toluene solution (4 liters) containing 504 g (4.2 mol) of acetophenone (1a) as a ketone and 485 g (4.0 mol) of (S)-1-phenylethylamine ((S)-2a) as an optically active primary amine, followed by heating under reflux for 20 hr and by removing water (formed as a by-product) with a Dean-Stark tube during the reaction, in order to conduct the reaction. Then, 564 g (4.0 mol) of fluoral-ethylhemiacetal (4a) were is dropped to the reaction liquid by spending 80 minutes at a temperature of not higher than 5° C., followed by stirring at 20° C. for 24 hr, thereby conducting the reaction. Then, 4-liter of 1N HCl were added to the reaction liquid, followed by stirring at room temperature for 1 hr. then washing with 2-liter of water, then concentration, and then vacuum drying, thereby obtaining 797 g of (R)-4,4,4-trifluoro-3-hydroxy-1-phenyl-1-butanone ((R)-5aa, purity: 71%). Its optical purity was found to be 59% ee by a chiral HPLC (DAICEL AS, n-hexane:i-propanol=95:5, 254 nm).

EXAMPLE 1-31

At first, 5.5 g (40 mmol) of zinc chloride were added to a toluene solution (4 liters) containing 649 g (4.2 mol) of 4-chloroacetophenone (1b) as a ketone and 484 g (4.0 mol) of (S)-1-phenylethylamine ((S)-2a) as an optically active primary amine, followed by heating under reflux for 20 hr and by removing water (formed as a by-product) with a Dean-Stark tube during the reaction, in order to conduct the reaction. Then, 564 g (4.0 mol) of fluoral-ethylhemiacetal (4a) were dropped to the reaction liquid by spending 80 minutes at a temperature of not higher than 5° C., followed by stirring at 25–26° C. for 24 hr, thereby conducting the reaction. Then, 4-liter of 1N HCl were added to the reaction liquid, followed by stirring at room temperature for 1 hr, then washing with 2-liter of water, then concentration, and then vacuum drying, thereby obtaining 999 g of (R)-4,4,4-trifluoro-3-hydroxy-1-(4-chlorophenyl)-1-butanone ((R)-5ba, purity: 72%). Its optical purity was found to be 54% ee by the chiral HPLC as that of Example 1-30

EXAMPLE 1-32

Recovery and Reuse of (R)-1-Phenylethylamine

A hydrochloric acid aqueous solution layer obtained by the post-treatment (the addition of 12 ml of 1.5 N HCl followed by stirring for 1 hr at room temperature) of Example 1-8 was made basic with 1N sodium hydroxide aqueous solution, followed by extraction with ethyl acetate, then washing with saturated brine, then drying with sodium sulfate anhydride, then filtration, then concentration, and then vacuum drying, thereby recovering a crude product. This crude product was distilled under vacuum, thereby recovering (R)-1-phenylethylamine ((R)-2a, 0.4 mmol, 80%). This optically active primary amine was found to have an optical purity of 98.5% ee (R). It was confirmed that results equivalent to those of Examples 1-1 and 1-8 were obtained by sequentially repeating Examples 1-1 and 1-8 using the recovered optically active primary amine of Example 1-32.

The following Examples 2-1 to 2-6 including Examples 2-2a and 2-2b are illustrative of the second process.

EXAMPLE 2-1

In this example, a recrystallization solvent was used, but racemic seed crystals were not added.

At first, 15.9 mg of 4,4,4-trifluoro-3-hydroxy-1-phenyl-1-butanone (43% ee, R) were dissolved in 0.8 ml of n-hexane (50 ml/g) with heating, followed by standing still for 3 hr at room temperature and then for 12 hr at 5° C. Optical purity of the resulting supernatant was found to be 85% ee (R). The precipitated crystals were separated by filtration, followed by washing with n-hexane, then vacuum drying, and then optical purity determination. The result was 4% ee (R). The above optical purity determinations were conducted by a chiral HPLC analysis (DAICEL OD-H, n-hexane:i-propanol=95:5, 254 nm).

The optical purity determinations conducted in the following Examples 2-2 to 2-6 including Examples 2-2a and 2-2b were the same as that of Example 2-1.

EXAMPLE 2-2

In this example, a recrystallization solvent was used, but racemic seed crystals were not added.

At first, 165.3 mg of 4,4,4-trifluoro-3-hydroxy-1-phenyl-1-butanone (88% ee, R) were dissolved in 5 ml of n-hexane (30 ml/g) with heating, followed by standing still for 3 hr at room temperature and then for 12 hr at 5° C. Optical purity of the resulting supernatant was found to be 94% ee (R).

EXAMPLE 2-2a

In this example, a recrystallization solvent was used, but racemic seed crystals were not added.

At first, 797 g of 4,4,4-trifluoro-3-hydroxy-1-phenyl-1-butanone (59% ee, R) were dissolved in 3985 ml (5 ml/g) of a mixture of toluene and n-heptane (toluene:n-heptane=1:6) with heating, followed by standing still for 3 hr at room temperature and then for 12 hr at 5° C. The precipitated crystals were separated by filtration, followed by washing with 797 ml (1 ml/g) of n-heptane and then vacuum drying, thereby collecting 570 g of crystals and 242 g of a mother liquor concentrate. The crystals and the concentrate were respectively found to have optical purities of 6% ee (R) and 95% ee (R). The theoretical recovery of the R-form was 98%.

EXAMPLE 2-2b

In this example, a recrystallization solvent was used, but racemic seed crystals were not added.

At first, 41.1 g of 4,4,4-trifluoro-3-hydroxy-1-phenyl-1-butanone (6% ee, R) were dissolved in 205.5 ml (5 ml/g) of a mixture of toluene and n-heptane (toluene:n-heptane=1:10) with heating, followed by standing still for 3 hr at room temperature and then for 12 hr at 5° C. The precipitated crystals were separated by filtration, followed by washing with 41 ml (1 ml/g) of n-heptane and then vacuum drying, thereby collecting 38.2 g of crystals and 2.9 g of a mother liquor concentrate. The crystals and the concentrate were respectively found to have optical purities of 0% ee (R) and 91% ee (R).

EXAMPLE 2-3

In this example, a recrystallization solvent was not used, and racemic seed crystals were not added.

At first, 2 g of 4,4,4-trifluoro-3-hydroxy-1-phenyl-1-butanone (60% ee, R) were dissolved in 3 ml of ethyl acetate with heating. The resulting solution was allowed to stand still in an open system for 3 days at room temperature, while the ethyl acetate was allowed to evaporate. After that, optical purity of an oil-like, crystal-free residue was determined. The result was 85% ee (R). The precipitated crystals were separated by filtration, followed by washing with n-hexane, then vacuum drying, and then optical purity determination. The result was 1% ee (R).

EXAMPLE 2-4

In this example, a recrystallization solvent was used, and racemic seed crystals were added.

At first, 1.82 g of 4,4,4-trifluoro-3-hydroxy-1-phenyl-1-butanone (31% ee, R) were dissolved in 36.4 ml (20 ml/g) of n-hexane with heating. While the resulting solution was under a heated condition, 18.2 mg (1/100 weight) of the racemic seed crystals were added to the solution, followed by standing still for 2.5 hr at room temperature. The precipitated crystals were separated by filtration, followed by washing with 9.1 ml (5 ml/g) of n-hexane and then vacuum drying, thereby collecting 1.33 g of crystals and 0.53 g of mother liquor concentrate. These crystals and concentrate were found to respectively have optical purities of 6% ee (R) and 95% ee (R). The theoretical recovery of the R-form was 91%.

EXAMPLE 2-5

In this example, a recrystallization solvent was used, and racemic seed crystals were added.

At first, 1.32 g of 4,4,4-trifluoro-3-hydroxy-1-phenyl-1-butanone (6% ee, R) were dissolved in 39.5 ml (30 ml/g) of n-hexane with heating. While the resulting solution was under a heated condition, 13.2 mg (1/100 weight) of the racemic seed crystals were added to the solution, followed by standing still for 3 days at room temperature. Optical purity of the resulting supernatant was found to be 63% ee (R). The precipitated crystals were separated by filtration, followed by washing with 9.9 ml (7.5 ml/g) of n-hexane and then vacuum drying, thereby collecting 1.18 g of crystals and 0.14 g of a mother liquor concentrate. These crystals and concentrate were found to respectively have optical purities of 0.2% ee (R) and 57% ee (R). The theoretical recovery of the R-form is greater than 95%.

EXAMPLE 2-6

In this example, a recrystallization solvent was used, and racemic seed crystals were added.

At first, 0.14 g of 4,4,4-trifluoro-3-hydroxy-1-phenyl-1-butanone (57% ee, R) were dissolved in 4.1 ml (30 ml/g) of n-hexane with heating. While the resulting solution was under a heated condition, 1.4 mg (1/100 weight) of the racemic seed crystals were added to the solution, followed by a first standing still for 2.5 hr at room temperature. Optical purity of the resulting supernatant was found to be 95% ee (R). After the first standing still, a second standing still was conducted for 12.8 hr at 5° C. Then, optical purity of the resulting supernatant was found to be 96% ee (R). After the second standing still, a third standing still was conducted for 4.5 hr at −15° C. Then, optical purity of the resulting supernatant was found to be 97% ee (R).

The following Examples 3-1 to 3-3 are illustrative of the third process. In these examples, the absolute configuration of optically active 4,4,4-trifluoro-3-hydroxy-1-aryl-1-butanone was determined by comparing the sign (+or −) of the measured value of the optical rotation with that of the published data. Furthermore, the enantiomeric excess ratio is represented by %ee, as recited above, and is determined by chiral liquid chromatography (DAICEL OD-H or AS). Still furthermore, chemical purity of all of the after-mentioned compounds was determined by gas chromatography (CP-Chirasil-DeX CB).

EXAMPLES 3-1–3-3

In each of these examples, an optically active aryl butanone derivative represented by the general formula [4] ((R)-1-a (X═H), optical purity: 290% ee) was purified as follows.

At first, as shown in Table 4, 5 g of (R)-4,4,4-trifluoro-3-hydroxy-1-phenyl-1-butanone were dissolved in n-hexane at 65° C. by heating. Then, to the resulting solution 0.05 g (1/100 weight) of optically pure seed crystals (100% ee) of the R-form were added under room temperature, followed by standing still for 2 days. The precipitated crystals were separated by filtration, followed by washing with a small amount of n-hexane and then vacuum drying, thereby collecting crystals having a structure represented by the following formula [16] and a mother liquor.

[16]

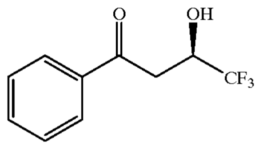

The results are shown in Table 4. The recovery was determined in view of the chemical purity and the optical purity.

TABLE 4

| | Before Purification | | | Crystals after Purification | | | Mother Liquor After Purification | |
|---|---|---|---|---|---|---|---|---|
| | Optical Purity (% ee) | Chem. Purity (%) | Solvent | Optical Purity (% ee) | Chem. Purity (%) | Recovery (%) | Optical Purity (% ee) | Chem. Purity (%) |
| Ex. 3-1 | 95.8(R) | 99.1 | n-hexane (40 ml/g) | 99.8(R) | 99.7 | 54 | 91.6(R) | 98.5 |
| Ex. 3-2 | 93.9(R) | 98.5 | n-hexane (40 ml/g) | 99.6(R) | 100 | 41 | 90.6(R) | 96.6 |
| Ex. 3-3 | 93.9(R) | 98.5 | n-hexane (30 ml/g) | 99.3(R) | 100 | 47 | 89.7(R) | 95.9 |

Referential Example 3-1

In this referential example, an optically active aryl butanone derivative represented by the general formula [4] ((R)-1-a (X═H), optical purity: ≦90% ee) was purified as follows.

At first, 1.1 g of (R)-4,4,4-trifluoro-3-hydroxy-1-phenylbutanone (chemical purity: 98.7%; optical purity: 49.5% ee) were dissolved in 45 ml (40 ml/g) of n-hexane at 65° C. by heating. Then, to the resulting solution 0.0055 g (1/200 weight) of optically pure seed crystals (100% ee) of the R-form were added under room temperature, followed by standing still for 2 days. The precipitated crystals were separated by filtration, followed by washing with a small amount of n-hexane and then vacuum drying, thereby collecting 0.7 g of crystals having a structure represented by the formula [16] and 0.4 g of a mother liquor. The crystals were found to have a chemical purity of 99.7% and an optical purity of 25.1% ee (R). The recovery determined in view of chemical purity and optical purity was 67%. The mother liquor was found to have a chemical purity of 97.7% and an optical purity of 94.0% ee (R).

The following Referential Example 3-2 according to the present invention is illustrative of the fourth process (Baeyer-Villiger oxidation).

Referential Example 3-2

At first, 2 g (9.17 mmol, 1 eq.) of (R)-4,4,4-trifluoro-3-hydroxy-1-phenyl-1-butanone (chemical purity: 99.7%; optical purity: 99.8% ee) obtained by the recrystallization according to Example 3-1 were dissolved in 20 ml of methylene chloride, thereby preparing a butanone derivative solution.

Separately, 15.41 g (73.39 mmol, 8 eq.) of trifluoroacetic anhydride were dissolved in 20 ml of methylene chloride, followed by the addition of 1.56 g (27.52 mmol, 3 eq.) of 60% hydrogen peroxide aqueous solution at 0° C. and then stirring for 15 min at room temperature, thereby preparing a trifluoroperacetic acid solution.

Then, 20 ml of the trifluoroperacetic acid solution were added at 0° C. to the above butanone derivative solution, followed by stirring at room temperature for 24 hr, then neutralization with a saturated sodium hydrogencarbonate aqueous solution, then extraction with methylene chloride, then washing with saturated brine, then drying with magnesium sulfate anhydride, then filtration, then concentration, and then vacuum drying, thereby obtaining 1.82 g of a crude product having a structure represented by the following formula [17]. The yield was 85%, and the optical purity was 99.8% ee (R).

[17]

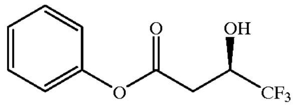

The following Examples 4-1–4-4 are illustrative of the fourth process (Baeyer-Villiger oxidation) using peroxophosphoric acid as an oxidizing agent.

EXAMPLE 4-1

(1) Preparation of Peroxophosphoric Acid

At first, 568 mg (4 mmol, 4 eq.) of phosphorus pentoxide were suspended in 2 ml of acetonitrile. Then, 227 mg (4 mmol, 4 eq.) of 60% hydrogen peroxide aqueous solution was added to the suspension under cooling with ice, followed by stirring for 1 hr at the same temperature and then for 2 hr at room temperature, thereby obtaining a peroxophosphoric acid solution which is colorless, transparent and homogeneous.

(2) Baeyer-Villiger Oxidation (X═H)

To the obtained peroxophosphoric acid solution 218 mg (1 mmol, 95% ee, R) of 4,4,4-trifluoro-3-hydroxy-1-phenyl-1-butanone in the form of solid were added under cooling with ice, followed by stirring for 2 hr at room temperature. The remaining peroxophosphoric acid was decomposed with 4 ml of 1N sodium sulfite aqueous solution, followed by addition of 20 ml of a saturated sodium hydrogencarbonate aqueous solution, then extraction with 20 ml of ethyl acetate twice, then washing with 20 ml of saturated brine, then drying with magnesium sulfate anhydride, then filtration, then concentration, and then vacuum drying) thereby obtaining 217 mg of crystals having a yellowish white color. The chemical purity of the crystals was found to be 98.3% by gas chromatography. The chemical yield in view of chemical purity was 91.0%. The optical purity was found to be 95% ee (R) by a chiral HPLC analysis (DAICEL OD-H, n-hexane:i-propanol=95:5, 220 nm). The NMR spectrum of the crystals was as follows.

$^1$H-NMR (TMS, ppm, $CDCl_3$); 2.95 (dd, J=8.1, 16.2 Hz, 1H), 3.02 (dd, J=4.2, 16.2 Hz, 1H), 8.19 (broad, 1H), 4.50–4.63 (m, 1H), 7.10 (d, J=7.7 Hz, 2H), 7.27 (t, J=7.7 Hz, 1H), 7.41 (t, J=7.7 Hz, 2H)

EXAMPLE 4-2

(1) Preparation of Peroxophosphoric Acid

A peroxophosphoric acid solution was prepared by the same steps as those of Example 4-1.

(2) Baeyer-Villiger Oxidation (X═H)

To the obtained peroxophosphoric acid solution under cooling with ice 10 mg (0.1 mmol, 0.1 eq.) of sulfuric acid and then 218 mg (1 mmol) of 4,4,4-trifluoro-3-hydroxy-1-phenyl-1-butanone (95% ee, R) in the form of solid were added, followed by stirring for 1 hr at room temperature. Then, the same steps as those of Example 4-1 were conducted, thereby obtaining 224 mg of crystals having a yellowish white color. The chemical purity of the crystals was found to be 98.5% by gas chromatography. The chemical yield in view of chemical purity was 94.2%. The optical purity was found to be 95% ee (R) by the same chiral HPLC analysis as that of Example 4-1. The NMR spectrum of the crystals was the same as that of Example 4-1.

EXAMPLE 4-3

(1) Preparation of Peroxophosphoric Acid

A peroxophosphoric acid solution was prepared by the same steps as those of Example 4-1.

(2) Baeyer-Villiger Oxidation (X═H)

To the obtained peroxophosphoric acid solution under cooling with ice 253 mg (1 mmol) of 4,4,4-trifluoro-3-hydroxy-1-p-chlorophenyl-1-butanone (chemical purity: 98.1%, optical purity: 97% ee, R) in the form of solid were added, followed by stirring for 3 hr at room temperature. Then, the same steps as those of Example 4-1 were conducted, thereby obtaining 233 mg of crystals having a yellowish white color. The chemical purity of the crystals was found to be 95.7% by gas chromatography. The chemical yield in view of chemical purity was 84.6%. The optical purity was found to be 97% ee (R) by a chiral HPLC analysis (DAICEL CHIRAL PACK AS, n-hexane:i-propanol=90:10, 225 nm). The NMR spectrum of the crystals was as follows.

$^1$H-NMR (TMS, ppm, $CDCl_3$);2.94 (dd, J=8.0, 16.8 Hz, 1H), 3.00 (dd, J=3.6, 16.8 Hz, 1H), 3.11 (broad, 1H), 4.56 (m, 1H), 7.06 (d, J=8.8 Hz, 2H), 7.36 (d, J=8.8 Hz, 2H)

EXAMPLE 4.4

(1) Preparation of Peroxophosphoric Acid

At first, 5.41 g (38.1 mmol, 3 eq.) of phosphorus pentoxide were suspended in 25.4 ml of acetonitrile. Then, 2.16 g (38.1 mmol, 3 eq.) of 60% hydrogen peroxide aqueous solution was added to the suspension under cooling with ice, followed by stirring for 1 hr at the same temperature and then for 2 hr at room temperature, thereby obtaining a peroxophosphoric acid solution which is colorless, transparent and homogeneous.

(2) Baeyer-Villiger Oxidation (X═H)

To the obtained peroxophosphoric acid solution 2.87 g (12.7 mmol) of 4,4,4-trifluoro-3-hydroxy-1-phenyl-1-butanone (95% ee, R) in the form of solid were added under cooling with ice, followed by stirring for 5 hr at room temperature. The remaining peroxophosphoric acid was decomposed with 25 ml of 1N sodium sulfite aqueous solution, followed by addition of 25 ml of a saturated sodium hydrogencarbonate aqueous solution, then extraction with 20 ml of ethyl acetate two times, then washing with 20 ml of saturated brine, then drying with magnesium sulfate anhydride, then filtration, then concentration, and then vacuum drying, thereby obtaining 2.73 g of crystals having a yellowish white color. The chemical purity of the crystals was found to be 94.6% by gas chromatography. The chemical yield in view of chemical purity was 87.0%. The optical purity was found to be 95% ee (R) by the same chiral HPLC analysis as that of Example 4-1. The NMR spectrum of the crystals was the same as that of Example 4-1.

The following Examples 5-1–5-19 and 5-20–5-21 are illustrative of the sixth and seventh processes, respectively. In these Examples 5-1–5-21, the absolute configuration of optically active 4,4,4-trifluoro-1,3-butanediol was determined by comparing the sign (+ or −) of the measured value of the optical rotation with that of the published data. Furthermore, the absolute configuration of an optically active 4,4,4-trifluoro-3-hydroxybutyric acid aryl ester was determined after reducing this ester into the optically active butanediol by sodium borohydride. As mentioned above, the enantiomeric excess ratio is represented by % ee. The optical purity of the optically active 4,4,4-trifluoro-3-hydroxybutyric acid aryl ester and that of dibenzoate of the optically active 4,4,4-trifluoro-1,3-butanediol were determined by chiral liquid chromatography (DAICEL OD-H or AS). Still furthermore, chemical purity of all of the after-mentioned compounds was determined by gas chromatography (CP-Chirasil-DeX CB) or $^1$H-NMR.

EXAMPLES 5-1–5-12

In each of these examples, as shown in Table 5, 2.5 g of (R)-4,4,4-trifluoro-3-hydroxybutyric acid phenyl ester (chemical purity: 93.4%, optical purity: 94.8% ee) were dissolved in n-hexane (in case of Examples 6-1 and 5-2) or a mixture of n-hexane and toluene (in case of Examples 5-3–5-12) at 65° C. with heating, followed by addition of seed crystals of this ester under room temperature and then standing still for 2 days. Then, the precipitated crystals were separated by filtration, followed by washing with a small amount of n-hexane and then vacuum drying, thereby collecting crystals having a structure represented by the formula [17] and a mother liquor. The results are shown in Table 5, and the recovery was determined in view of chemical purity and optical purity.

TABLE 5

| | | Crystals | | Optical Purity of |
|---|---|---|---|---|
| | Solvent | Optical Purity (% ee) | Recovery (%) | Mother Liquor (% ee) |
| Ex. 5-1 | n-hexane (40 ml/g) | 97.7 (R) | 72 | 85.6 (R) |
| Ex. 5-2 | n-hexane (10 ml/g) | 95.2 (R) | 2 | 88.4 (R) |
| Ex. 5-3 | n-hexane/toluene = 10/1 (10 ml/g) | 95.4 (R) | — | 88.5 (R) |
| Ex. 5-4 | n-hexane/toluene = 5/1 (10 ml/g) | 98.0 (R) | 82 | 82.1 (R) |
| Ex. 5-5 | n-hexane/toluene = 4/1 (10 ml/g) | 98.2 (R) | 64 | 87.1 (R) |

TABLE 5-continued

| | Solvent | Crystals Optical Purity (% ee) | Crystals Recovery (%) | Optical Purity of Mother Liquor (% ee) |
|---|---|---|---|---|
| Ex. 5-6 | n-hexane/toluene = 3/1 (10 ml/g) | 98.2 (R) | 55 | 88.4 (R) |
| Ex. 5-7 | n-hexane/toluene = 2/1 (10 ml/g) | 98.5 (R) | 48 | 91.0 (R) |
| Ex. 5-8 | n-hexane/toluene = 5/1 (5 ml/g) | 97.8 (R) | 77 | 84.3 (R) |
| Ex. 5-9 | n-hexane/toluene = 4/1 (5 ml/g) | 96.9 (R) | 79 | 87.2 (R) |
| Ex. 5-10 | n-hexene/toluene = 3/1 (5 ml/g) | 97.8 (R) | 70 | 87.4 (R) |
| Ex. 5-11 | n-hexane/toluene = 2/1 (5 ml/g) | 98.1 (R) | 68 | 86.7 (R) |
| Ex. 5-12 | n-hexane/toluene = 1/1 (5 ml/g) | 98.6 (R) | 42 | 91.8 (R) |

EXAMPLE 5-13

At first, 115.5 g of (R)-4,4,4-trifluoro-3-hydroxybutyric acid phenyl ester (chemical purity: 93.4%, optical purity: 94.80% ee) were dissolved in a mixture of n-hexane and toluene (n-hexane:toluene=5:1) at 65° C. with heating, followed by addition of 115.5 mg (1/1,000 weight) of seed crystals of this ester at 45° C. and then standing still for 16 hr under room temperature. Then, the precipitated crystals were separated by filtration, followed by washing with a small amount of n-hexane and then vacuum drying, thereby collecting 78 g of crystals having a structure represented by the formula [17] and 37.8 g of a mother liquor. The crystals were found to have a chemical purity of 99.6% and an optical purity of 98.0% ee (R). The recovery of the crystals in view of chemical purity and optical purity was 72%. The mother liquor was found to have a chemical purity of 82.2% and an optical purity of 85.7% ee (R).

EXAMPLES 5-14–5-17

In each of these examples, as shown in Table 6, 2.5 g of (R)-4,4,4-trifluoro-3-hydroxybutyric acid phenyl ester (chemical purity: 93.4%, optical purity: 94.8% ee) were dissolved in n-hexane (in case of Examples 5-14 and 5-17) or a mixture of n-hexane and toluene (in case of Examples 5-15 and 5-16) at 65° C. with heating, followed by stirring for 2 days. Then, the precipitated crystals were separated by filtration, followed by washing with a small amount of n-hexane and then vacuum drying, thereby collecting crystals having a structure represented by the formula [17] and a mother liquor. The results are shown in Table 6, and the recovery was determined in view of chemical purity and optical purity.

TABLE 6

| | Solvent | Crystals Optical Purity (% ee) | Crystals Recovery (%) | Optical Purity of Mother Liquor (% ee) |
|---|---|---|---|---|
| Ex. 5-14 | n-hexane (10 ml/g) | 97.2 (R) | 86 | 82.3 (R) |
| Ex. 5-15 | n-hexane/toluene = 10/1 (10 ml/g) | 97.2 (R) | 84 | 80.7 (R) |
| Ex. 5-16 | n-hexane/toluene = 5/1 (10 ml/g) | 97.3 (R) | 78 | 84.1 (R) |
| Ex. 5-17 | n-hexane (5 ml/g) | 95.0 (R) | — | 88.0 (R) |

EXAMPLE 5-18

At first, 14.9 g of (R)-4,4,4-trifluoro-3-hydroxybutyric acid p-chlorophenyl ester (chemical purity: 79.2%, optical purity: 94.7% ee) were dissolved in 75 ml (5 ml/g) of n-hexane at 65° C. with heating, followed by stirring for 6 hr under room temperature. Then, the precipitated crystals were separated by filtration, followed by washing with a small amount of n-hexane and then vacuum drying, thereby collecting 10.1 g of crystals having a structure represented by the following formula [18] and 5 g of a mother liquor.

[18]

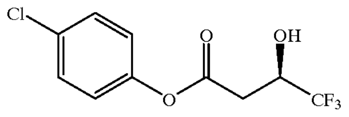

The crystals were found to have a chemical purity of 98.8% and an optical purity of 99.9% ee (R). The recovery of the crystals in view of chemical purity and optical purity was 86%. The mother liquor was found to have a chemical purity of 27.9% and an optical purity of 55.6% ee (R).

EXAMPLE 5-19

At first, 9 g of (R)-4,4,4-trifluoro-3-hydroxybutyric acid p-chlorophenyl ester (chemical purity: 56.8%, optical purity: 87.1% ee) were dissolved in 45 ml (5 ml/g) of n-hexane at 65° C. with heating, followed by stirring for 6 hr under room temperature. Then, the precipitated crystals were separated by filtration, followed by washing with a small amount of n-hexane and then vacuum drying, thereby collecting 2.5 g of crystals having a structure represented by the formula [18] and 5.9 g of a mother liquor. The crystals were found to have a chemical purity of 98.7% and an optical purity of 99.8% ee (R). The recovery of the crystals in view of chemical purity and optical purity was 52%. The mother liquor was found to have a chemical purity of 36.1% and an optical purity of 70.6% ee (R).

EXAMPLE 5-20

Reduction of (R)-1-a (X=H) by Sodium Borohydride 14.1 g (333 mmol, 1 eq.) of sodium borohydride (purity: 90%) were suspended in 300 ml of tetrahydrofuran to prepare a suspension. Separately, 78 g (333 mmol, 1 eq.) of (R)-4,4,4-trifluoro-3-hydroxybutyric acid phenyl ester (chemical purity: 99.6%, optical purity: 98.0% ee) obtained by the recrystallization of Example 5-13 were dissolved in 200 ml of tetrahydrofuran to prepare a solution. Then, this solution was dropped to the suspension by spending about 1 hr, while the temperature of the suspension was maintained at a temperature not higher than 50° C., followed by stirring for 1 hr under room temperature and then for 2 hr under reflux. Each of these steps from the suspending of sodium borohydride to the stirring for 2 hr under reflux was conducted under an atmosphere of argon. After the reaction, 200 ml of water were added to the reaction liquid under cooling with ice, followed by stirring for 2 hr under reflux. Then, tetrahydrofuran was distilled off under vacuum to concentrate the reaction liquid, followed by extraction with t-butyl methyl ether, then drying with magnesium sulfate anhydride, then filtration, then concentration, and then vacuum drying, thereby obtaining a crude product of (R)-4,4,4-trifluoro-1,3-butanediol having a structure represented by the following formula [19], with a quantitative yield.

[19]

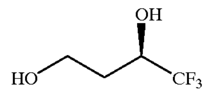

The crude product was purified by separating phenols therefrom, thereby obtaining 40.8 g of a purified product of (R)-4,4,4-trifluoro-1,3-butanediol (total yield: 85%). This purification was possible by a rectification using about five stages. The purified product was found to have a chemical purity of 99.4% and an optical purity of 98.1% ee (R). In fact, its optical purity was determined by a chiral liquid chromatography using a dibenzoate derived from the purified product.

EXAMPLE 5-21

Reduction of (R)-1-b (X=Cl) by Sodium Borohydride

Under an atmosphere of argon, 8.4 g (200 mmol, 1 eq.) of sodium borohydride (purity: 90%) were suspended in 180 ml of tetrahydrofuran to prepare a suspension. Separately, 53.7 g (200 mmol, 1 eq.) of (R)-4,4,4-trifluoro-3-hydroxybutyric acid p-chlorophenyl ester (chemical purity: 99.3%, optical purity: 99.9% ee) obtained by a recrystallization similar to that of Example 5-18 were dissolved in 120 ml of tetrahydrofuran to prepare a solution. Then, this solution was dropped to the suspension by spending about 40 min, while the temperature of the suspension was maintained at a temperature not higher than 50° C., followed by stirring for 1 hr under room temperature and then for 2 hr under reflux. After the reaction, 120 ml of water were added to the reaction liquid under cooling with ice, followed by stirring for 2 hr under reflux. Then, tetrahydrofuran was distilled off under vacuum to concentrate the reaction liquid, followed by extraction with t-butyl methyl ether, then drying with magnesium sulfate anhydride, then filtration, then concentration, and then vacuum drying, thereby obtaining a crude product of (R)-4,4,4-trifluoro-1,3-butanediol having a structure represented by the formula [19], with a quantitative yield. The crude product was purified by separating p-chlorophenols therefrom, thereby obtaining 23.9 g of a purified product of (R)-4,4,4-trifluoro-1,3-butanediol (total yield: 83%). This purification was possible by a rectification using about 20 stages. The purified product was found to have a chemical purity of 98.9% and an optical purity of 99.9% ee (R). Its optical purity was determined by the same manner as that of Example 5-20.

The following Examples 6-1–6-3 and 6-4–6-5 are respectively illustrative of the fourth and fifth processes each using trifluoroperacetic acid as an oxidizing agent.

EXAMPLE 6-1

A trifluoroperacetic acid solution was prepared by dissolving 749 mg (3.57 mmol, 8 eq.) of trifluoroacetic anhydride in 1.5 ml of methylene chloride, followed by addition of 78 mg (1.38 mmol, 3 eq.) of 60% hydrogen peroxide aqueous solution at 0° C. and then stirring for 15 min at room temperature. Then, 100 mg (0.46 mmol, 1 eq.) of 4,4,4-trifluoro-3-hydroxy-1-phenyl-1-butanone (92% ee, R) were dissolved in 1.5 ml of methylene chloride, followed by addition of 1.5 ml of the trifluoroperacetic acid solution at 0° C. and then stirring for 1 hr at 0° C., thereby conducting the reaction. After this stirring, the reaction liquid was neutralized with a saturated sodium hydrogencarbonate, followed by extraction is with methylene chloride, then washing with saturated brine, then drying with magnesium sulfate anhydride, then filtration, then concentration, and then vacuum drying, thereby obtaining 101.7 mg of a crude product. The conversion was found to be 87% by $^1$H-NMR analysis. Its optical purity was found to be 92% ee (R) by a chiral HPLC analysis (DAICEL OD-H, n-hexane:i-propanol=95:5, 220 nm). Its NMR spectrum was as the same as that of Example 4-1.

EXAMPLE 6-2

At first, 20 mg (0.092 mmol, 1 eq.) of 4,4,4-trifluoro-3-hydroxy-1-phenyl-1-butanone (98% ee, R) were dissolved in 1 ml of methylene chloride, followed by addition of 135 mg (0.642 mmol, 7 eq.) of trifluoroacetic anhydride and 10 mg (0.092 mmol, 1 eq.) of 30% hydrogen peroxide aqueous solution at 0° C., and then stirring for 12 hr at room temperature. After this stirring, the reaction liquid was neutralized with a saturated sodium hydrogencarbonate, followed by the same steps as those of Example 6-1, thereby quantitatively obtaining a crude product. The conversion was found to be >95% by $^1$H-NMR analysis.

EXAMPLE 6-3

A trifluoroperacetic acid solution was prepared by dissolving 3.98 g (18.96 mmol, 8 eq.) of trifluoroacetic anhydride in 5 ml of methylene chloride, followed by addition of 414 mg (7.30 mmol, 3 eq.) of 60% hydrogen peroxide aqueous solution at 0° C. and then stirring for 15 min at room temperature. Then, 530 mg (2.43 mmol, 1 eq.) of 4,4,4-trifluoro-3-hydroxy-1-phenyl-1-butanone (95% ee, R) were dissolved in 5 ml of methylene chloride, followed by addition of 5 ml of the trifluoroperacetic acid solution at 0° C. and then stirring for 24 hr at room temperature, thereby conducting the reaction. After this stirring, the reaction liquid was neutralized with a saturated sodium hydrogencarbonate, followed by the same steps as those of Example 6-1, thereby obtaining 894 mg of a crude product. The conversion was found to be >95% by $^1$H-NMR analysis. Its optical purity was found to be 95% ee (R) by the same chiral HPLC analysis as that of Example 6-1.

EXAMPLE 6-4

At first, 180 mg (1.58 mmol, 3 eq.) of trifluoroacetic acid and then 1 ml of a solution containing 109 mg (0.50 mmol, 1 eq.) of a racemic mixture of 4,4,4-trifluoro-3-hydroxy-1-phenyl-1-butanone dissolved in methylene chloride were added at room temperature to 28 mg (0.49 mmol, 1 eq.) of 60% hydrogen peroxide aqueous solution, followed by stirring for 40 hr at room temperature. After this stirring, the reaction liquid was neutralized with a saturated sodium hydrogencarbonate, followed by the same steps as those of Example 6-1, thereby obtaining 116 mg of a crude product. The conversion was found to be 66% by gas chromatography (CP-Chirasil-Dex CB, FID).

EXAMPLE 6-5

At first, 690 mg (6.05 mmol, 6 eq.) of trifluoroacetic acid and then 2 ml of a solution containing 218 mg (1.00 mmol, 1 eq.) of a racemic mixture of 4,4,4-trifluoro-3-hydroxy-1-phenyl-1-butanone dissolved in methylene chloride were added at room temperature to 112 mg (1.98 mmol, 2 eq.) of 60% hydrogen peroxide aqueous solution, followed by stirring for 72 hr at room temperature. After this stirring, the reaction liquid was neutralized with a saturated sodium hydrogencarbonate, followed by the same steps as those of Example 6-1, thereby obtaining 176 mg of a crude product. The conversion was found to be 99% by the same gas chromatography as that of Example 6-4.

The following Examples 6-6–6-7 are illustrative of the eighth process (ester exchange).

EXAMPLE 6-6

At first, 26.7 mg (0.114 mmol, 1 eq.) of phenyl 4,4,4-trifluoro-3-hydroxybutyrate (95% ee, R) were dissolved in 3 ml of methanol, followed by addition of 2.9 mg (0.015 mmol, 0.1 eq.) of p-toluenesulfonic acid monohydrate (p-TsOH.$H_2O$) and then stirring for 16.5 hr with heating under reflux. Then, methanol was distilled out in order to concentrate the reaction liquid, followed by neutralization with a saturated sodium hydrogencarbonate, then extraction with ethyl acetate, then washing with saturated brine, then drying with magnesium sulfate anhydride, then filtration, then concentration, and then vacuum drying, thereby quantitatively obtaining a crude product. The conversion was found to be >95% by $^1$H-NMR analysis. The optical purity was found to be 96% ee (R) by a chiral GC analysis (CP-Chirasil-Dex CB, FID).

EXAMPLE 6-7

At first, 17 mg (0.074 mmol, 1 eq.) of phenyl 4,4,4-trifluoro-3-hydroxybutyrate (95% ee, R) were dissolved in 3 ml of ethanol, followed by addition of 5 mg (0.026 mmol, 0.4 eq.) of p-TsOH.$H_2O$ and then stirring for 42 hr with heating under reflux. Then, ethanol was distilled out in order to concentrate the reaction liquid, followed by neutralization with 0.25 N NaOH aqueous solution, then extraction with ethyl acetate, then washing with saturated brine, then drying with magnesium sulfate anhydride, then filtration, then concentration, and then vacuum drying, thereby quantitatively obtaining a crude product. The conversion and the optical purity were found to be 75% and 95% ee (R) by the same chiral GC analysis as that of Example 6-6.

The entire disclosure of each of Japanese Patent Application Nos. 2000-019156 filed on Jan. 27, 2000, 2000-019165 filed on Jan. 27, 2000, 2000-034026 filed on Feb. 10, 2000, 2000-198316 filed on Jun. 27, 2000, 2000-208742 filed on Jul. 10, 2000, and 2000-817069 filed on Oct. 17, 2000, including specification, claims and summary, is incorporated herein by reference in its entirety.

What is claimed is:

1. A process for increasing optical purity of an optically active 4,4,4-trifluoro-3-hydroxy-1-aryl-1-butanone derivative represented by the formula [1], said process comprising the sequential steps of:

(a) dissolving said derivative in a recrystallization solvent that is n-hexane or a mixture of toluene and n-heptane with heating to prepare a solution, said recrystallization solvent being in an amount of from 5 ml to 50 ml per gram of said derivative;

(b) allowing said solution to stand still at a temperature within a range of from room temperature to −15° C., thereby precipitating racemic crystals of said derivative, from said solution; and (c) removing said racemic crystals from said solution obtained by the step (b), thereby obtaining said derivative that is dissolved in said solution obtained by the step (b) and that has an optical purity higher than that of said derivative of the step (a),

[1]

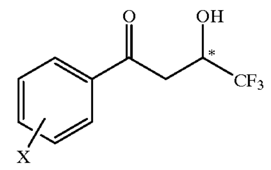

where X is a hydrogen, a $C_{1-6}$ alkyl, a $C_{1-6}$ alkoxy, or a halogen atom selected from the group consisting of F, Cl, Br and I; and the symbol * represents an asymmetric carbon, wherein, when said recrystallization solvent is the mixture of toluene and n-heptane, a relative proportion of said toluene to said n-heptane is in a range of from 1:10 to 1:6.

2. A process according to claim 1, wherein the step (b) is conducted in the presence of racemic seed crystals of said derivative.

3. A process according to claim 1, wherein the steps (b) and (c) are sequentially repeated, thereby further increasing optical purity of said derivative that is dissolved in said solution obtained by the step (b).

4. A process according to claim 1, wherein said X of the formula [1] is a hydrogen.

5. A process for increasing optical purity of an optically active 4,4,4-trifluoro-3-hydroxy-1-aryl-1-butanone derivative represented by the formula [1], said process comprising the sequential steps of:

(a) dissolving said derivative in ethyl acetate with heating to prepare a solution;

(b) allowing said solution to stand still in an open system to evaporate the ethyl acetate, thereby obtaining a product in which racemic crystals of said derivative are precipitated; and (c) removing said racemic crystals from the product of the step (b), thereby obtaining said derivative that has an optical purity higher than that of said derivative of the step (a),

[1]

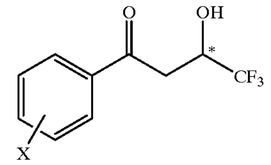

wherein X is a hydrogen, a $C_{1-6}$ alkyl, a $C_{1-6}$ alkoxy, or a halogen atom selected from the group consisting of F, C1, Br and I; and the symbol * represents an asymmetric carbon.

6. A process for increasing optical purity of an optically active 4,4,4-trifluoro-3-hydroxy-1-aryl-1-butanone derivative represented by the formula [1], said process comprising the steps of:

(a) dissolving said derivative, which has a first optical purity of 90% ee or greater, in n-hexane to prepare a solution; and (b) adding optically pure seed crystals of said derivative to said solution, said optically pure seed crystals having an optical purity of 99% ee or greater, thereby recrystallizing said derivative from said solution in a form of crystals having a second optical purity that is higher than said first optical purity,

[1]

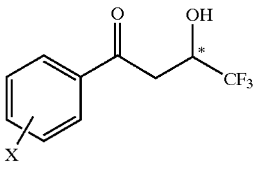

where X is a hydrogen, a $C_{1-6}$ alkyl, a $C_{1-6}$ alkoxy, or a halogen atom selected from the group consisting of F, Cl, Br and I; and the symbol * represents an asymmetric carbon.

7. A process according to claim 6, wherein the step (a) is conducted by using said n-hexane in an amount of from 30 ml to 40 ml per gram of said derivative.

8. A process according to claim 6, wherein the step (a) is conducted at a temperature of about 65° C., and the step (b) is conducted at room temperature.

9. A process according to claim 6, wherein said X of the formula [1] is a hydrogen.

10. A process according to claim wherein said seed crystals of said derivative have an optical purity of 100% ee.

11. A process according to claim 6, wherein said derivative is in an R-form or S-form with respect to stereochemistry.

12. A process according to claim 11, wherein said derivative is in an R-form with respect to stereochemistry.

13. A process for increasing optical purity of an optically active 4,4,4-trifluoro-3-hydroxy-1-aryl-1-butanone derivative represented by the formula [1], said process comprising the sequential steps of:

(a) dissolving said derivative, which has a first optical purity less than 90% ee, in a recrystallization solvent that is n-hexane or a mixture of toluene and n-heptane under heating to prepare a first solution, said recrystallization solvent being in an amount of from 5 ml to 50 ml per gram of said derivative;

(b) allowing said first solution to stand still at a temperature within a range of from room temperature to −15° C., thereby precipitating racemic crystals of said derivative, from said first solution;

(c) removing said racemic crystals from said first solution obtained by the step (b), thereby obtaining a second solution in which said derivative having a second optical purity of 90% ee or higher is dissolved; and (d) adding optically pure seed crystals of said derivative to said second solution, said seed crystals having an optical purity of 99% ee or greater, thereby recrystallizing said derivative from said second solution in a form of crystals having a third optical purity that is higher than said second optical purity,

[1]

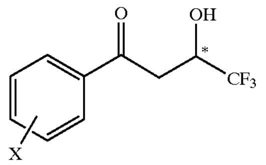

where X is a hydrogen, a $C_{1-6}$ alkyl, a $C_{1-6}$ alkoxy, or a halogen atom selected from the group consisting of F, Cl, Br and I; and the symbol * represents an asymmetric carbon, wherein, when said recrystallization solvent of the step (a) is the mixture of toluene and n-heptane, a relative proportion of said toluene to said n-heptane is in a range of from 1:10 to 1:6.

14. A process for increasing optical purity of an optically active 4,4,4-trifluoro-3-hydroxybutanic aryl ester derivative represented by the formula [1], said process comprising the sequential steps of:

(a) dissolving said derivative, which has a first optical purity, in a recrystallization solvent that is n-hexane or a mixture of n-hexane and toluene with heating to prepare a solution, said recrystallization solvent being in an amount of from 5 ml to 40 ml per gram of said derivative; and (b) allowing said solution to stand still at room temperature, thereby recrystallizing said derivative from said solution in a form of crystals having a second optical purity that is higher that said first optical purity,

[1]

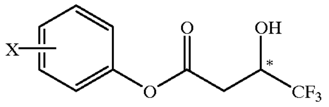

where X is a hydrogen, a $C_{1-6}$ alkyl, a $C_{1-6}$ alkoxy, or a halogen atom selected from the group consisting of F, Cl, Br, and I; and the symbol * represents an asymmetric carbon, wherein, when said recrystallization solvent of the step (a) is the mixture of n-hexane and toluene, a relative proportion of said n-hexane to said toluene is in a range of from 1:1 to 10:1.

15. A process according to claim 14, wherein said first optical purity is in a range of from about 87% ee to about 95% ee.

16. A process according to claim 14, wherein said X of the formula [1] is a hydrogen.

17. A process according to claim 14, wherein the step (a) is conducted at a temperature of about 65° C.

18. A process according to claim 14, wherein said derivative is in an R-form or S-form with respect to stereochemistry.

19. A process according to claim 18, wherein said derivative is in an R-form with respect to stereochemistry.

20. A process according to claim 14, wherein the step (b) is conducted in the presence of seed crystals of said derivative.

21. A process for increasing optical purity of an optically active compound represented by the Formula,

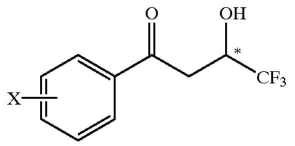

or

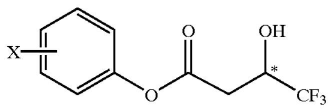

wherein X is a hydrogen, a $C_{1-6}$ alkyl, a $C_{1-6}$ alkoxy, or a halogen atom selected from the group consisting of F, Cl, Br and I; and the symbol * represents an asymmetric carbon, said process comprising the sequential steps of:

(a) dissolving same compound, which has a first optical purity, in a recrystallization solvent that is n-hexane with heating to prepare a solution, said recrystallization solvent being in an amount of about 40 ml per gram of said compound; and (b) allowing said solution to stand still at room temperature in the presence of seed crystals of said compound, thereby recrystallizing said compound from said solution in a form of crystals having a second optical purity that is higher than said first optical purity.

* * * * *